United States Patent [19]

Hartmann et al.

[11] Patent Number: 4,548,923
[45] Date of Patent: Oct. 22, 1985

[54] MURAMYL PEPTIDES AND PROCESSES FOR THEIR MANUFACTURE

[75] Inventors: Albert Hartmann, Grenzach, Fed. Rep. of Germany; Oskar Wacker, Basel; Gerhard Baschang, Bettingen, both of Switzerland; Lajos Tarcsay, Grenzach-Wyhlen, Fed. Rep. of Germany

[73] Assignee: Ciba Geigy Corporation, Ardsley, N.Y.

[21] Appl. No.: 608,911

[22] Filed: May 9, 1984

Related U.S. Application Data

[63] Continuation of Ser. No. 515,836, Jun. 21, 1983, abandoned.

[30] Foreign Application Priority Data

Jun. 23, 1982 [CH] Switzerland .................. 4527/82

[51] Int. Cl.$^4$ .................. A61K 37/00; C07D 333/32
[52] U.S. Cl. .................. 514/8; 525/54.11
[58] Field of Search .................. 260/112.5 R; 424/177; 514/8; 525/54.11

[56] References Cited

U.S. PATENT DOCUMENTS 4,323,560  4/1982  Baschang et al. ............ 260/112.5 R
4,414,204  11/1983  Tarcsay et al. ............ 260/112.5 R

FOREIGN PATENT DOCUMENTS 4775679  12/1979  Australia .
6068     12/1979  European Pat. Off. .
0025495  3/1981   European Pat. Off. .
0056992  4/1982   European Pat. Off. .

OTHER PUBLICATIONS

U.S. application 283,759.
U.S. application 340,680.

Primary Examiner—Delbert R. Phillips
Attorney, Agent, or Firm—Irving N. Feit; Irving M. Fishman

[57] ABSTRACT

The compounds of the formula I

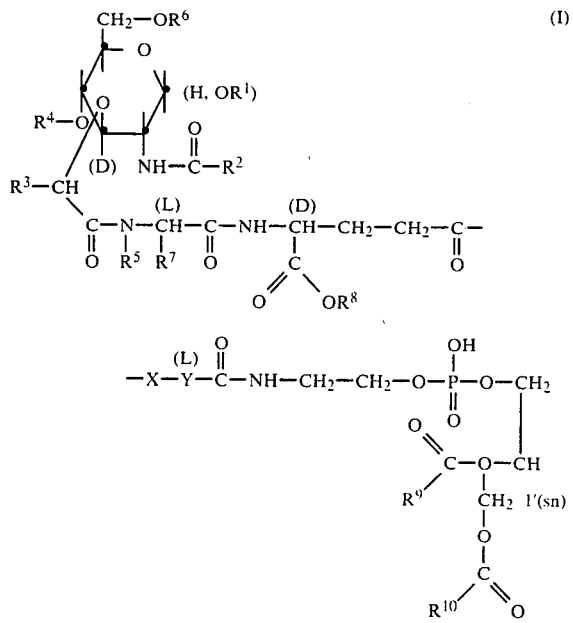

in which each of $R^1$, $R^4$ and $R^6$, independently of the others, represents hydrogen or lower alkanoyl, $R^2$ represents $C_{1-4}$-alkyl, hydroxymethyl or phenyl, $R^3$ represents hydrogen or methyl, $R^5$ represents hydrogen or $C_{1-3}$-alkyl, $R^7$ represents $C_{1-3}$-alkyl that is unsubstituted or substituted by hydroxy, mercapto or methylthio, $R^8$ represents hydrogen or lower alkyl, X represents oxygen or the group NH, Y represents $C_{1-4}$-alkylidene, and each of $R^9$ and $R^{10}$, independently of the other, represents $C_{11-17}$-alkyl or $C_{11-17}$-alkenyl, and their salts, have an immunostimulating activeity.

17 Claims, No Drawings

MURAMYL PEPTIDES AND PROCESSES FOR THEIR MANUFACTURE

This application is a continuation of application Ser. No. 515,836, filed 6/21/83, abandoned.

The invention relates to compounds of the formula I

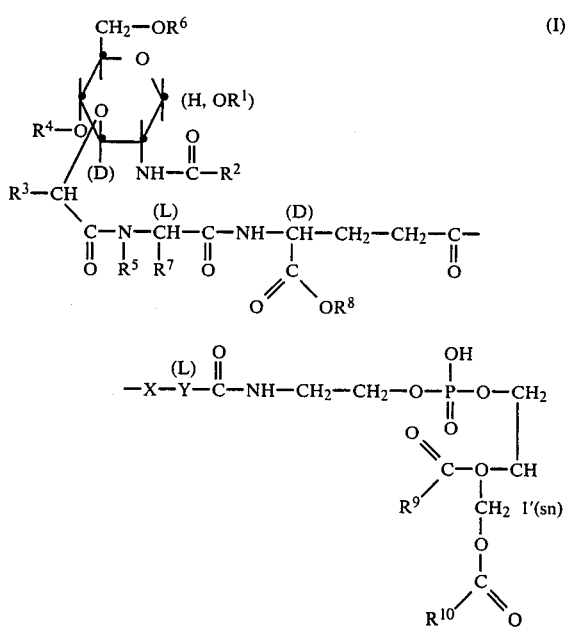

in which each of $R^1$, $R^4$ and $R^6$, independently of the others, represents hydrogen or lower alkanoyl, $R^2$ represents $C_{1-4}$-alkyl, hydroxymethyl or phenyl, $R^3$ represents hydrogen or methyl, $R^5$ represents hydrogen of $C_{1-3}$-alkyl, $R^7$ represents $C_{1-3}$-alkyl that is unsubstituted or substituted by hydroxy, mercapto or methylthio, $R^8$ represents hydrogen or lower alkyl, X represents oxygen or the group NH, Y represents $C_{1-4}$-alkylidene, and each of $R^9$ and $R^{10}$, independently of the other, represents $C_{11-17}$-alkyl or $C_{11-17}$-alkenyl, and to the salts of these compounds, to processes for their manufacture, to pharmaceutical preparations that contain these compounds, and to the use of the compounds of the formula I and their salts.

In the case of asymmetric substitution the compounds of the formula I have the (D)-configuration at $\underline{C}$—$R^3$, the (L)-configuration at $\underline{C}$—$R^7$, the (D)-configuration at $\underline{C}$—C—$OR^8$, the (L)-configuration in the radical Y and the α- and/or β-configuration at C-1 of the D-glucose radical, that is to say that the compounds of the formula I can be present as pure anomers or as anomeric mixtures.

For the characterisation of the configuration at the central C-atom of the glycerine moiety, there is used in accordance with the IUPAC rules the stereo-specific numbering of the C-atoms of the glycerine moiety, characterised by the prefix "sn". The uppermost C-atom in the Fischer projection of the vertical carbon chain, the hydroxy group at C-2 being towards the left, is given the number 1. In the compounds according to the invention the phosphoric acid group is bonded to C-atom 3 according to the stereospecific numbering.

The prefix "lower" used hereinbefore and hereinbelow denotes radicals having from and including 1 up to and including 7, especially from 1 to 4, carbon atoms.

Lower alkanoyl is, for example, propionyl, butyryl or hexanoyl, especially acetyl.

Lower alkyl is, for example, n-propyl, n-butyl, isobutyl, sec.-butyl, tert.-butyl, and also n-pentyl, n-hexyl or n-heptyl, especially methyl, ethyl or isopropyl.

In particular, an alkyl radical $R^2$ is especially methyl if $R^3$ represents methyl, or ethyl if $R^3$ represents hydrogen, an alkyl radical $R^5$ represents especially methyl, an alkyl radical $R^7$ represents especially methyl, ethyl or isopropyl, and an alkyl radical $R^8$ represents especially $C_{1-4}$-alkyl, especially straight-chain $C_{1-4}$-alkyl, more especially n-butyl.

$C_{1-3}$-alkyl $R^7$ substituted by hydroxy, mercapto or methylthio, is especially hydroxymethyl or 1-hydroxyethyl, mecaptomethyl or 2-methylthioethyl.

An alkylidene radical Y is a bivalent radical in which both bonds originate from the same C-atom, preferably a 1,1-linked radical, such as especially methylene or ethylidene, and also propylidene or isobutylidene.

A $C_{11-17}$-alkyl radical $R^9$ or $R^{10}$ is a straight-chain or branched, but especially straight-chain, radical, more especially a straight-chain radical having an uneven number of C-atoms, such as n-undecyl or n-tridecyl, more especially a straight-chain $C_{15-17}$-alkyl radical having an uneven number of C-atoms, that is to say n-heptadecyl or, especially, n-pentadecyl.

A $C_{11-17}$-alkenyl radical $R^9$ or $R^{10}$ is especially hepta-8(Z)-decenyl.

The proton bonded via oxygen to the phosphorus atom is acidic and can readily be removed with bases and replaced by a different cation. Therefore, at a pH value of 7, all or a majority of the compounds of the formula I are in salt form. The invention relates also to these salts and the acid/salt mixtures. The invention relates especially to pharmaceutically acceptable, non-toxic salts of the compounds of the formula I. These are especially metal or ammonium salts, such as alkali metal and alkaline earth metal salts, for example sodium, potassium, magnesium or calcium salts, and ammonium salts or salts with suitable organic amines, such as lower alkylamines, for example triethylamine. For isolation or purification purposes it is also possible to use pharmaceutically unacceptable salts, but only the pharmaceutically acceptable, non-toxic salts are used therapeutically, and these are therefore preferred.

The compounds according to the invention in which $R^1$, $R^4$ and $R^6$ represent hydrogen fall within the general scope of the European Patent Application having the publication number 0025 495 and, like the compounds of the formula I in which $R^1$, $R^4$ and/or $R^6$ represent lower alkanoyl, can be used as immunostimulators. In comparison with the compounds prior-published in the above-mentioned application, the compounds according to the invention have markedly reduced undesirable side-effects, and in particular they are much less, that is to say practically not at all, pyrogenic. This discovery is of great importance since the administration of a pyrogenic substance can occasionally result in thermal shock, for which reason safe use is ensured only under constant medical supervision and certain administration forms, such as intravenous administration, must remain out of the question.

The test for pyrogenity can be carried out in rabbits in accordance with the instructions given in European Pharmacopoeia, Vol. 2, pages 56–59 (1971). According to this test, even, for example, in the case of subcutaneous administration of a high dose, such as 30 mg/kg of the sodium salt of N-acetylmuramyl-L-alanyl-D-glutamyl-($C_\alpha$)-n-butyl ester-($C_\gamma$)-L-alanine-2-(1,2-dipalmitoyl-sn-glycero-3-hydroxyphosphoryloxy)-ethylamide (compound I), no pyrogenic effect can be observed.

In contrast, the same dose of the sodium salt of N-acetylmuramyl-L-alanyl-D-isoglutaminyl-L-alanine-2-(1,2-dipalmitoyl-sn-glycero-3-hydroxyphosphoryloxy)-ethylamide is highly pyrogenic.

The compounds according to the invention can be used as described in European Patent Application No. 00 25 495.

Because of their excellent tolerability they are, however, especially suitable for the prophylaxis and treatment of infectious diseases, a strong action occurring not only in the case of bacterial causative organisms but, surprisingly, also against viral causative organisms. The latter discovery has not been described hitherto and is of great practical significance, since hitherto a completely inadequate number of pharmaceuticals for curing diseases caused by viruses have been available. Especially noteworthy is the long prophylactic or therapeutic duration of action of from many days up to several weeks after a single administration of the compounds according to the invention and the broad spectrum of viral causative organisms against which the compounds are effective.

The muramyl peptides of the formula I can be used especially for the prophylaxis and treatment of diseases that are caused by the viruses listed in detail below [for the nomenclature see J. L. Melnick, *Prog. med. Virol.*, 26, 214–232 (1980) and 28, 208–221 (1982)]:

DNA viruses with cubic symmetry and naked nucleocapsid, DNA viruses with enveloped virion and also RNA viruses with cubic, and those with helical, symmetry of the capsid.

Preferably, the compounds of the formula I are used in the case of DNA viruses with enveloped virion and cubic symmetry of the capsid, in the case of RNA viruses with cubic symmetry of the capsid and naked virion and in the case of RNA viruses with helical symmetry of the capsid, in which the nucleocapsid casing is located at the surface membrane, but also in the case of Adenoviridae, Poxviridae and Coronaviridae, such as, especially, human coronaviruses.

The compounds of the formula I are used especially in the case of Herpetoviridae, Picornaviridae and myxoviruses, but also in the case of mastadenoviruses, such as, especially, human adenoviruses, in the case of Chordopoxvirinae, such as, chiefly, orthopoxviruses, such as, especially, for example, vaccinal viruses, in the case of Reoviridae, chiefly (especially human) rotaviruses, and also in the case of Caliciviridae and Rhabdoviridae, such as, especially, vesiculoviruses in humans as well as horses, cows and pigs.

The compounds of the formula I are mainly used in the case of Alphaherpetovirinae, rhinoviruses, cardioviruses and Orthomyxoviridae, but also in the case of Betaherpetovirinae, such as, especially, human cytomegaloviruses, in the case of aphthoviruses, especially aphthoviruses of cloven-hoofed animals, such as, chiefly, cows, and in the case of Paramyxoviridae, such as, especially, pneumoviruses, for example respiratory syncytial viruses in humans, and such as, in addition, morbilliviruses or paramyxoviruses, such as, for example, human parainfluenza viruses, including Sendai viruses.

Above all the compounds of the formula I are used in the case of simplex viruses, for example human herpes simplex viruses of types 1 and 2, in the case of human encephelomyocarditis viruses and in the case of influenza viruses, such as mainly influenza A and influenza B viruses, for example the viruses mentioned in the Examples.

The muramyl peptides of the formula I can be used for the prophylaxis or treatment of virus infections by administering them enterally or parenterally, especially together with suitable adjuncts or carriers. Preferably they are applied to the mucous membrane, for example intranasally, rectally, vaginally or to the conjunctiva of the eye, or orally. The antiviral effect occurs, however, also if administered in other ways, for example subcutaneously, intravenously, intramuscularly or if applied to the skin.

The type of administration that is the most suitable depends, inter alia, on the nature of the particular virus, for example, in the case of respiratory viruses, intranasal administration is in many cases preferable. The dosage of the active ingredient depends, inter alia, on the species of warm-blooded animal, the defensive condition of the organism, the mode of administration and the nature of the virus.

The compounds according to the invention have the further very interesting property of inhibiting the formation of metastases in the case of some tumours, especially of the lung, as can be demonstrated experimentally in the B16-BL6-melanoma model and in the case of Lewis lung carcinoma, administration in liposomes being especially advantageous.

The present invention relates especially to compounds of the formula I in which at least one of the radicals $R^1$, $R^4$ and $R^6$ represents lower alkanoyl.

The invention relates especially to compounds of the formula I in which each of $R^1$, $R^4$ and $R^6$, independently of the others, represents hydrogen or $C_{1-3}$-alkanoyl, $R^2$ represents $C_{1-2}$-alkyl or hydroxymethyl, $R^3$ represents hydrogen or methyl, $R^5$ represents hydrogen or methyl, $R^7$ represents $C_{1-3}$-alkyl or hydroxymethyl, $R^8$ represents hydrogen or $C_{1-4}$-alkyl, X represents oxygen or the group NH, Y represents $C_{1-3}$-alkylidene and each of $R^9$ and $R^{10}$, independently of the other, represents straight-chain $C_{11-17}$-alkyl or decarbonyloleoyl, and their salts.

The invention relates especially to compounds of the formula I in which each of $R^1$, $R^4$ and $R^6$, independently of the others, represents hydrogen or acetyl, $R^2$ represents methyl or ethyl, $R^3$ represents hydrogen or methyl, $R^5$ represents hydrogen or methyl, $R^7$ represents $C_{1-3}$-alkyl, $R^8$ represents hydrogen or $C_{1-4}$-alkyl, X represents oxygen or the group NH, Y represents $C_{1-2}$-alkylidene and each of $R^9$ and $R^{10}$, independently of the other, represents straight-chain $C_{11-17}$-alkyl having an uneven number of C-atoms or decarbonyloleoyl, and their salts.

The invention relates especially to the above-mentioned compounds of the formula I in which $R^8$ represents one of the mentioned alkyl radicals, and/or in which $R^1$, $R^4$ and $R^6$ represent hydrogen, and their salts.

The invention relates especially to compounds of the formula I in which $R^1$, $R^4$ and $R^6$ represent hydrogen, $R^2$ represents methyl or ethyl, $R^3$ represents hydrogen if $R^2$ represents ethyl, or methyl if $R^2$ represents methyl, $R^5$ represents hydrogen or methyl, $R^7$ represents $C_{1-2}$-alkyl, $R^8$ represents straight-chain $C_{1-4}$-alkyl, X represents oxygen or the group NH, Y represents ethylidene and each of $R^9$ and $R^{10}$, independently of the other, represents straight-chain $C_{15-17}$-alkyl having an uneven number of C-atoms, and their salts.

The invention relates especially to the above-mentioned compounds of the formula I in which $R^3$ represents methyl, $R^5$ represents hydrogen, $R^8$ represents n-butyl, X represents the group NH and/or $R^9$ just as $R^{10}$ represents n-pentadecyl, and their salts, and the compounds of the formula I mentioned in the Examples.

The novel compounds of the formula I and their salts can be obtained according to methods that are known per se.

They may be obtained if (a) a compound of the formula II,

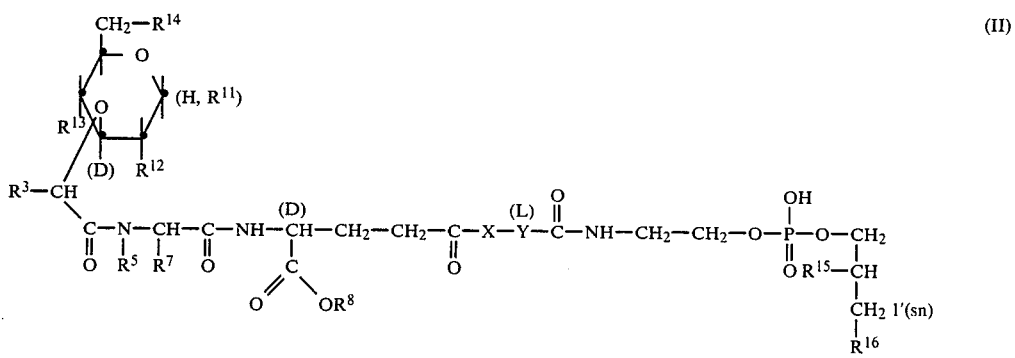

(II)

in which at least one of the radicals $R^{11}$, $R^{13}$, $R^{14}$, $R^{15}$ and $R^{16}$ represents hydroxy that is free or in reactive form, and/or in which $R^{12}$ represents amino that is free or in reactive form, and the remaining substituents have the meanings given above, with the proviso that functional groups present in a compound of the formula II, with the exception of the group(s) participating in the reaction, are optionally in protected form, is acylated with a carboxylic acid or a reactive derivative thereof, there being introduced at least one acyl radical

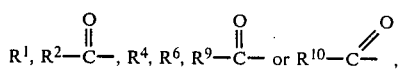

in which the substituents have the meanings given above, and any protecting groups present are removed, or (b) a compound of the formula III,

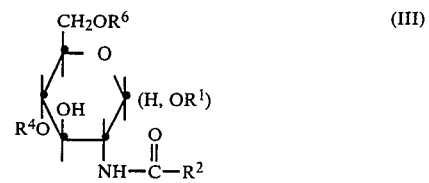

(III)

in which the substituents have the meanings given above and any functional groups present, with the exception of the free hydroxy group in the 3-position, are optionally in protected form, the 3-hydroxy group optionally being in reactive form, is reacted with a compound of the formula IV

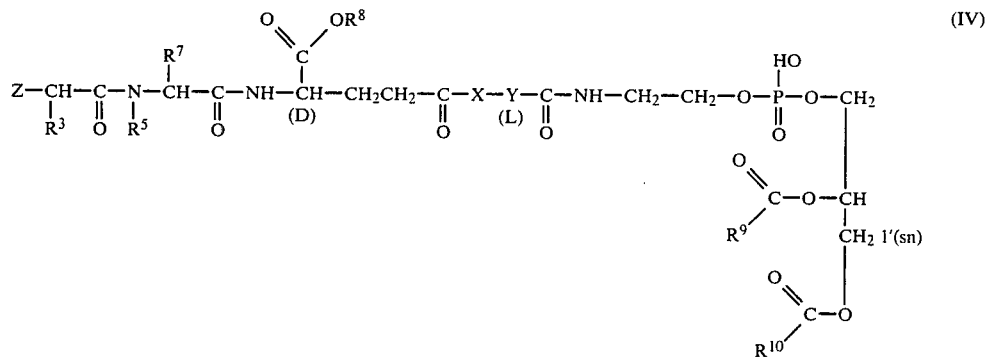

(IV)

in which Z represents a hydroxy group optionally present in reactive form and the remaining substituents have the meanings given above, with the proviso that functional groups present in a compound of the formula IV, with the exception of Z, are optionally in protected form, and any protecting groups present are removed, or (c) a compound of the formula V,

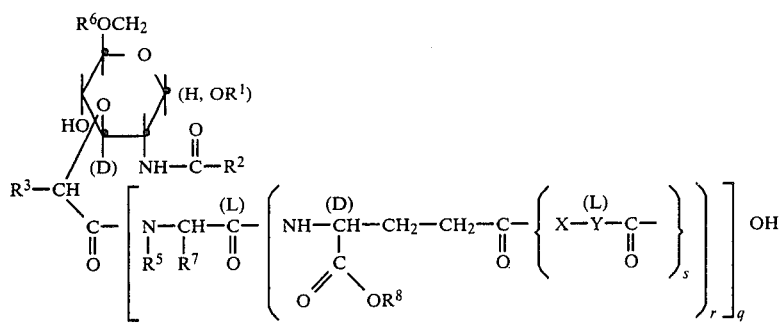
(V)

in which each of s, r and q, independently of the others, represents 0 or 1 and the substituents have the meanings given above, with the proviso that free functional groups present in a compound of the formula V, with the exception of the group participating in the reaction, are optionally in protected form, or a reactive carboxylic acid derivative thereof, is reacted with a compound of the formula VI,

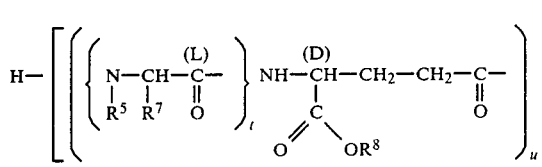
(VI)

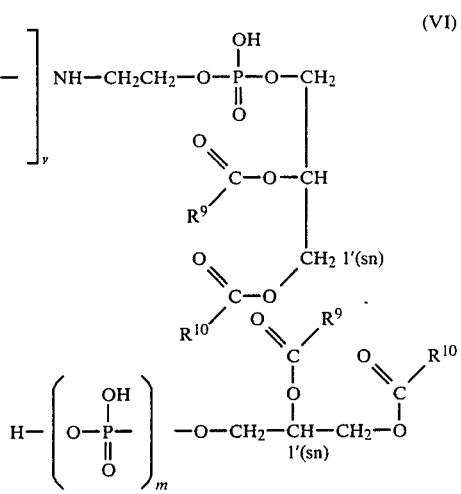

in which each of t, u and v, independently of the others, represents 0 or 1 and $R^8$ represents lower alkyl or a carboxy-protecting group, and the remaining substituents have the meanings given above, with the proviso that t, u and v each represents 1 if in the reactant of the formula V q represents 0, or that t represents 0, u represents 1 and v represents 1 if q represents 1 and r represents 0, or that u represents 0 and v represents 1 if q represents 1, r represents 1 and s represents 0, or that v represents 0 if q, r and s each represents 1, or with a reactive derivative thereof, and any protecting groups present are removed, or (d) a compound of the formula VII, participating in the reaction, are optionally in protected form, or a reactive phosphoric acid derivative of such an acid of the formula VII in which w represents 1, is reacted with a compound of the formula VIII (VIII)

in which the substituents have the meanings given above and m represents 0 or 1, with the proviso that m represents 1 if in the reactant of the formula VII w represents 0, or that m represents 0 if w represents 1, or with a reactive phosphoric acid derivative of an acid of the formula VIII in which m represents 1, and any protecting groups present are removed, or (VII)

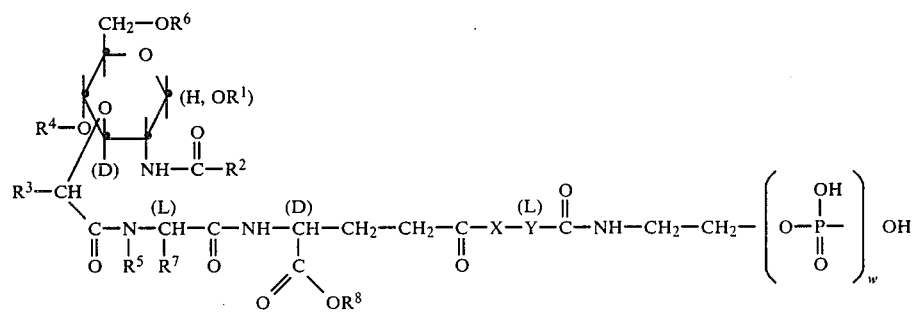

in which w represents 0 or 1 and the substituents have the meanings given above, with the proviso that any free functional groups, with the exception of the group (e) the reactive derivative of a compound of the formula VII,

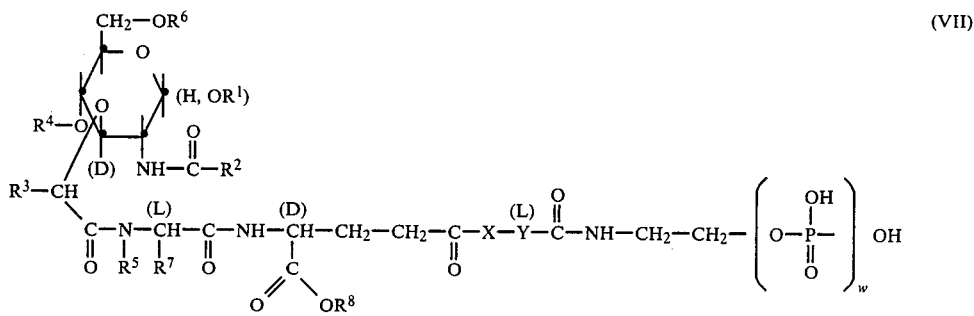
(VII)

in which w represents 0 or 1 and the substituents have the meanings given above, with the proviso that free functional groups present in a compound of the formula VII, with the exception of the group participating in the reaction, are optionally protected by readily removable protecting groups, and with the proviso that the reactive derivative of a compound of the formula VII in which w represents 0 is one having a reactive, esterified terminal hydroxy group, and with the proviso that the reactive derivative of a compound of the formula VII in which w represents 1 is a salt, is reacted with the reactive derivative of a compound of the formula VIII,

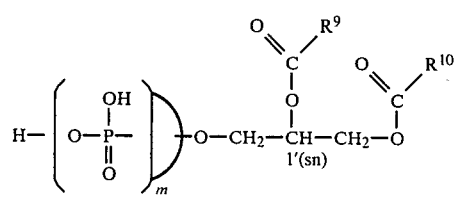
(VIII)

in which the substituents have the meanings given above and m represents 0 or 1, with the proviso that m represents 1 if in the reactant of the formula VII w represents 0, the reactive derivative of a compound of the formula VIII being a salt, or that m represents 0 if w represents 1, the reactive derivative of a compound of the formula VIII being one having a reactive, esterified terminal hydroxy group, and any protecting groups present are removed, or (f) a compound of the formula IX,

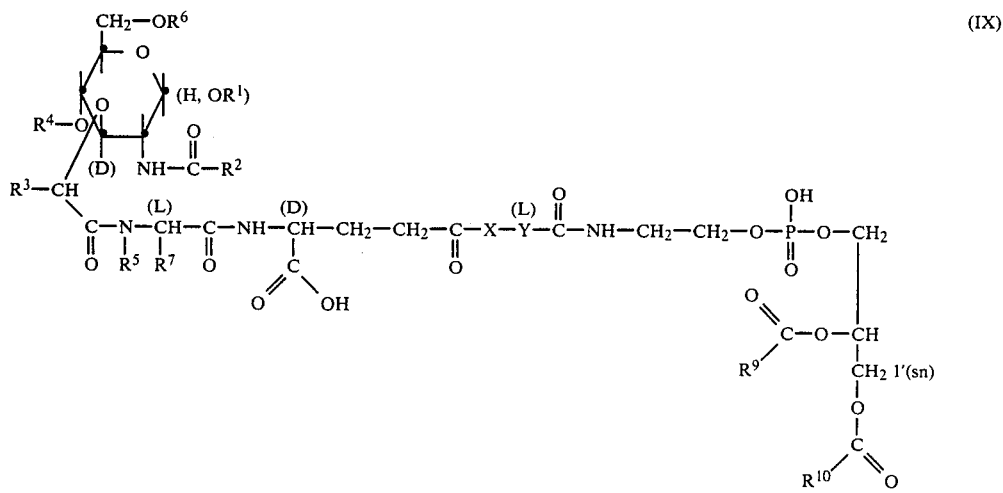
(IX)

in which the substituents have the above meanings, free functional groups present in a compound of the formula IX, with the exception of the group participating in the reaction, optionally being in protected form, or a reactive carboxylic acid derivative of a compound of the formula IX, is reacted with a lower alkanol $R^8$—OH in which $R^8$ represents lower alkyl, or with a reactive derivative thereof, and any protecting groups present are removed, or (g) a compound of the formula X,

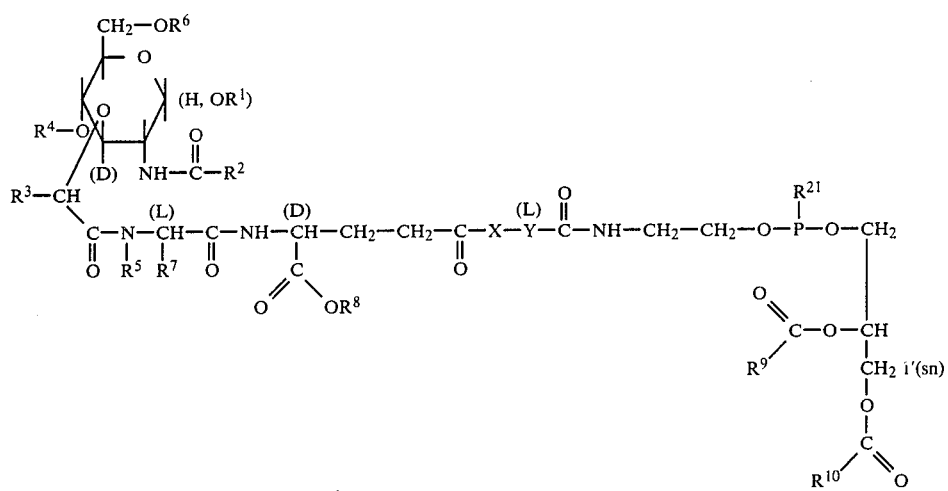
(X)

in which $R^{21}$ represents hydrogen or a protecting group and the remaining substituents have the meanings given above, free functional groups present in a compound of the formula I, with the exception of the group participating in the reaction, optionally being in protected form, or a tautomer of this compound, is oxidised with an oxidising agent, and any protecting groups present are removed, or (h) in a furanose compound of the formula XI,

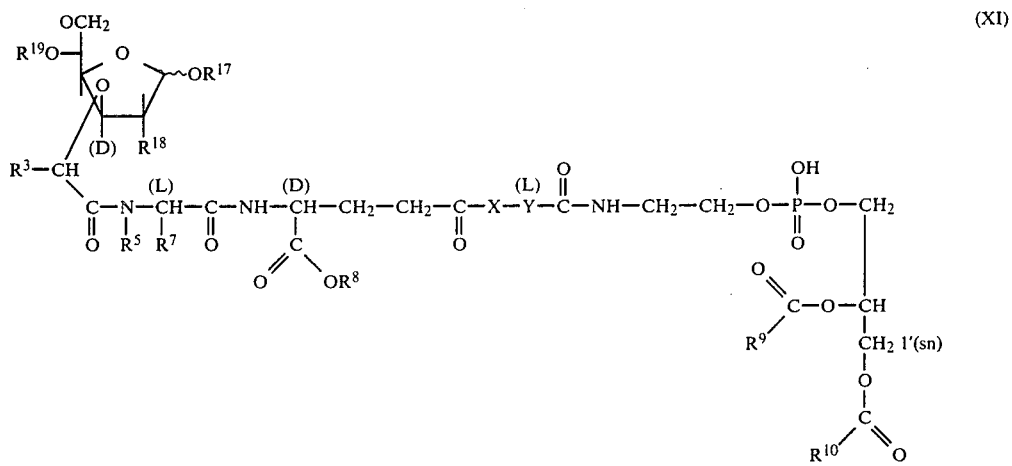
(XI)

in which $R^{17}$ represents hydrogen or a readily removable hydroxy-protecting group and $R^{18}$ has the meaning given above for the radical

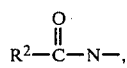

or $R^{17}$ and $R^{18}$ together represent a bivalent protecting group of the formula

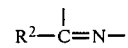

bonded by the free valency of the C-atom to oxygen, in which $R^2$ has the meaning given above, and $R^{19}$ and $R^{20}$ represent hydrogen or a readily removable hydroxy-protecting group, or $R^{19}$ and $R^{20}$ together represent a bivalent hydroxy-protecting group, and the remaining substituents have the meanings given above, the protecting groups are removed, or (i) in a compound of the formula I in which at least one of the radicals $R^1$, $R^2$, $R^4$, $R^6$, $R^7$ and $R^8$ is in protected form, the protecting group(s) is or are removed, or (j) a compound of the formula XII,

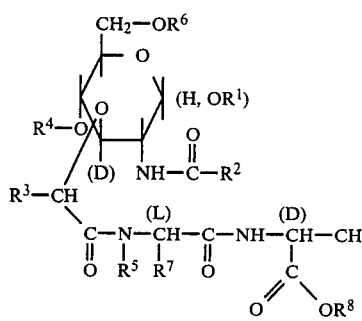
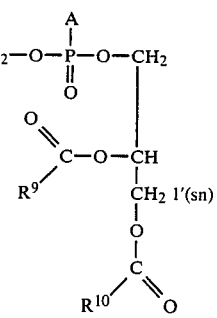

(XII)

in which A represents a halogen atom and the remaining substituents have the meanings given above, is hydrolysed, and, if desired, after carrying out one of the processes (a) to (j), a resulting compound of the formula I is converted into its salt or a resulting salt is converted into a different salt.

Process a (acylation)

Hydroxy $R^{11}$, $R^{13}$, $R^{14}$, $R^{15}$ or $R^{16}$ in reactive form is especially metaloxy or reactive esterified hydroxy.

Metaloxy is especially alkali metaloxy or alkaline earth metaloxy, more especially lithiumoxy, sodiumoxy or potassiumoxy.

Reactive esterified hydroxy is, for example, hydroxy esterified by a strong inorganic or organic acid, such as by a mineral acid, for example hydrohalic acid, such as hydrochloric, hydrobromic or hydriodic acid, also sulphuric acid, or halosulphuric acid, for example fluorosulphuric acid, or hydroxy esterified by a strong organic sulphonic acid, such as a lower alkanesulphonic acid optionally substituted, for example, by halogen, such as fluorine, or an aromatic sulphonic acid, for example a benzenesulphonic acid optionally substituted by lower alkyl, such as methyl, halogen, such as bromine, and/or by nitro, for example a methanesulphonic acid, trifluoromethanesulphonic or p-toluenesulphonic acid.

Amino present in reactive form is, for example, amino activated by reaction with a phosphite, such as diethyl chlorophosphite, ethylene chlorophosphite, 1,2-phenylene chlorophosphite, ethyl dichlorophosphite or tetraethyl pyrophosphite. A reactive amino group is, for example, also a carbamic acid halide or an isocyanate, the amino group being bonded to halocarbonyl, for example chlorocarbonyl, or being present as an isocyanate group, and in the latter case it is possible to obtain only compounds of the formula I that carry a hydrogen atom at the nitrogen atom of the amide group formed by the reaction.

The reactive derivative of a carboxylic acid is, for example, a salt, for example a caesium salt, if in the reactant of the formula II at least one hydroxy group is present in reactive esterified form, or is a reactive carboxylic acid ester, a reactive carboxylic anhydride or a cyclic amide. Reactive acid derivatives can also be formed in situ.

Activated esters of acids are especially esters that are unsaturated at the linking carbon atom of the esterifying radical, for example of the vinyl ester type, such as actual vinyl esters (which can be obtained, for example, by transesterification of a corresponding ester with vinyl acetate; activated vinyl ester method), carbamoylvinyl esters (which can be obtained, for example, by treatment of the corresponding acid with an isoxazolium reagent; 1,2-oxazolium or Woodward method), or 1-lower alkoxyvinyl esters (which can be obtained, for example, by treatment of the corresponding acid with a lower alkoxyacetylene; ethoxyacetylene method), or esters of the amidino type, such as N,N'-disubstituted amidino esters (which can be obtained, for example, by treatment of the corresponding acid with a suitable N,N'-disubstituted carbodiimide, for example, N,N'-dicyclohexyl carbodiimide; carbodiimide method), or N,N-disubstituted amidino esters (which can be obtained, for example, by treatment of the corresponding acid with an N,N-disubstituted cyanamide; cyanamide method), suitable aryl esters, especially phenyl esters suitably substituted by electron-attracting substituents (which can be obtained, for example, by treatment of the corresponding acid with a suitably substituted phenol, for example 4-nitrophenol, 4-methylsulphonylphenol, 2,4,5-trichlorophenol, 2,3,4,5,6-pentachlorophenol or 4-phenyldiazophenol, in the presence of a condensation agent, such as N,N'-dicyclohexyl carbodiimide; activated aryl esters method), cyanomethyl esters (which can be obtained, for example, by treatment of the corresponding acid with chloroacetonitrile in the presence of a base; cyanomethyl esters method), thioesters, especially phenylthioesters optionally substituted, for example, by nitro (which can be obtained, for example, by treatment of the corresponding acid with thiophenols that are optionally substituted, for example, by nitro, inter alia with the aid of the anhydride or carbodiimide method; activated thioesters method), or amino or amido esters (which can be obtained, for example, by treatment of the corresponding acid with an N-hydroxyamino or N-hydroxyamido compound, for example N-hydroxysuccinimide, N-hydroxypiperidine, N-hydroxyphthalimide or 1-hydroxybenzotriazole, for example according to the anhydride or carbodiimide method; activated N-hydroxy esters method).

Reactive anhydrides may be symmetric or preferably mixed anhydrides of these acids, thus, for example, anhydrides with inorganic acids, such as acid halides, especially acid chlorides (which can be obtained, for example, by treating the corresponding acid with thionyl chloride, phosphorus pentachloride or oxalyl chloride; acid chloride method), azides (which can be obtained, for example, from a corresponding acid ester by way of the corresponding hydrazide and the treatment of the latter with nitrous acid; azide method), anhydrides with carbonic acid semi-derivatives, such as with corresponding esters, for example carbonic acid lower alkyl semi-esters (which can be obtained, for example, by treating the corresponding acid with haloformic acid lower alkyl esters, such as chloroformic acid lower alkyl esters, or with a 1-lower alkoxycarbonyl-2-lower alkoxy-1,2-dihydroquinoline, for example 1-lower alkoxycarbonyl-2-ethoxy-1,2-dihydroquinoline; mixed O-alkylcarbonic acid anhydrides method), or anhydrides with dihalogenated, especially dichlorinated, phosphoric acid (which can be obtained, for example, by treating the corresponding acid with phosphorus oxychloride; phosphorus oxychloride method), or anhydrides with organic acids, such as mixed anhydrides with organic carboxylic acids (which can be obtained, for example, by treating the corresponding acid with an optionally substituted lower alkane-carboxylic acid halide or phenylalkanecarboxylic acid halide, for example phenylacetic acid chloride, pivalic acid chloride or trifluoroacetic acid chloride; mixed carboxylic acid anhydrides method) or with organic sulphonic acids (which can be obtained, for example, by treating a salt, such as an alkali metal salt, of the corresponding acid, with a suitable organic sulphonic acid halide, such as lower alkanesulphonic acid chloride or arylsulphonic acid chloride, for example methane- or p-toluene-sulphonic acid chloride; mixed sulphonic acid anhydrides method), and symmetric anhydrides (which can be obtained, for example, by condensing the corresponding acid in the presence of a carbodiimide or of 1-diethylaminopropine; symmetric anhydrides method).

Suitable cyclic amides are especially amides having five-membered diazacycles of aromatic character, such as amides with imidazoles, for example imidazole (which can be obtained, for example, by treating the corresponding acid with N,N'-carbonyldiimidazole; imidazolide method), or pyrazoles, for example 3,5-dimethylpyrazole (which can be obtained, for example, by way of the acid hydrazide by treatment with acetylacetone; pyrazolide method).

Protecting groups of optionally present functional groups are, for example, the protecting groups mentioned above.

The reaction may be carried out in a manner known per se, the reaction conditions depending especially on whether and how the carboxy group participating in the reaction has been activated, customarily in the presence of a suitable solvent or diluent or a mixture thereof, and, if necessary, in the presence of a condensation agent which, for example, if the carboxy group participating in the reaction is in the form of an anhydride, may also be an acid-binding agent, while cooling or heating, for example in a temperature range of from approximately −30° C. to approximately +150° C., in a closed reaction vessel and/or in the atmosphere of an inert gas, for example nitrogen. Customary condensation agents are, for example, carbodiimides, for example N,N'-diethyl, N,N'-dipropyl, N,N'-dicyclohexyl or N-ethyl-N'-(3-dimethylaminopropyl)carbodiimide, suitable carbonyl compounds, for example carbonyldiimidazole, or 1,2-oxazolium compounds, for example 2-ethyl-5-phenyl-1,2-oxazolium-3'-sulphonate and 2-tert.-butyl-5-methylisoxazolium perchlorate, or a suitable acylamino compound, for example 2-ethoxy-1-ethoxycarbonyl-1,2-dihydroquinoline. Customary acid-binding condensation agents are, for example, alkali metal carbonates or bicarbonates, for example sodium or potassium carbonate or bicarbonate (usually together with a sulphate), or organic bases, such as customarily sterically hindered tri-lower alkylamines, for example N,N-diisopropyl-N-ethylamime.

The reaction is preferably carried out in such a manner that an activated carboxylic acid ester or a reactive carboxylic acid anhydride or cyclic amide is reacted with a compound of the formula II in which the hydroxy and/or amino groups participating in the reaction are in free form.

Protecting groups, their introduction and the manner in which they are removed are described, for example, in "Protective Groups in Organic Chemistry", Plenum Press, London, New York 1973, and in "Methoden der organischen Chemie", Houben-Weyl, 4th Edition, Vol. 15/1, Georg-Thieme-Verlag, Stuttgart 1974. It is characteristic of protecting groups that they can be readily removed, i.e. without undesired secondary reactions taking place, for example by solvolysis, reduction, photolysis or alternatively under physiological conditions.

Hydroxy-protecting groups are, for example, acyl radicals, such as optionally substituted, for example halo-substituted, lower alkanoyl, such as 2,2-dichloroacetyl, or acyl radicals of carbonic acid semi-esters, especially tert.-butoxycarbonyl, optionally substituted benzyloxycarbonyl or diphenylmethoxycarbonyl, for example 4-nitrobenzyloxycarbonyl, or 2-halo-lower alkoxycarbonyl, such as 2,2,2-trichloroethoxycarbonyl, also trityl or formyl, such as organic silyl or stannyl radicals, also readily removable etherifying groups, such as tert.-lower alkyl, for example tert.-butyl, 2-oxa- or 2-thia-aliphatic or -cycloaliphatic hydrocarbon radicals, especially 1-lower alkoxy-lower alkyl or 1-lower alkylthio-lower alkyl, for example methoxymethyl, 1-methoxyethyl, 1-ethoxyethyl, 1-methylthiomethyl, 1-methylthioethyl or 1-ethylthioethyl, or 2-oxa- or 2-thia-cycloalkyl having 5 or 6 ring atoms, for example tetrahydrofuryl or 2-tetrahydropyranyl or corresponding thia analogues, and also optionally substituted 1-phenyl-lower alkyl, such as optionally substituted benzyl or diphenylmethyl, there being suitable as substituents of the phenyl radicals, for example, halogen, such as chlorine, lower alkoxy, such as methoxy, and/or nitro.

Process b (linking of the sugar moiety and side chain)

A compound of the formula III in which the 3-hydroxy group is in reactive form is, for example, a metaloxy compound, as can be obtained, for example, by reacting a compound of the formula III with a relatively strong base, such as an alkali metal hydride or amide, or a compound in which the 3-hydroxy group is in reactive esterified form, for example as described above.

The reaction is preferably carried out in such a manner that a 3-metaloxy compound of the formula III is reacted with a compound of the formula IV in which Z represents one of the reactive esterified hydroxy groups described above. In addition, a compound of the formula III in which the 3-hydroxy group is in reactive esterified form can alternately be reacted with a compound of the formula IV in which Z represents metaloxy as described above.

Process c ($S_n2_t$ reactions)

Reactive carboxylic acid derivatives of a compound of the formula V are reactive esters, anhydrides or amides analogous to those mentioned in Process (a).

As mentioned in (a), derivatives of acids of the formula V can also be formed in situ. Thus, for example, N,N'-disubstituted amidino esters can be formed in situ by reacting a mixture of the starting material of the formula VI and the acid of the formula V in the presence of a suitable N,N'-disubstituted carbodiimide, for example N,N'-dicyclohexyl carbodiimide. In addition, amino or amido esters of acids of the formula V can be formed in the presence of the starting material of the formula VI, which is to be acylated, by reacting a mixture of the corresponding acid and amino starting materials in the presence of an N,N'-disubstituted carbodiimide, for example N,N'-dicyclohexyl carbodiimide, and an N-hydroxyamine or N-hydroxyamide, for example N-hydroxysuccinimide, optionally in the presence of a suitable base, for example 4-dimethylaminopyridine.

A derivative of the compound of the formula VI in which the amino group participating in the reaction is in reactive form can be manufactured, for example, by reaction with a phosphite, for example one of those mentioned in Process (a). A reactive form of a compound of the formula VI is, for example, also a carbamic acid halide or an isocyanate, the amino group participating in the reaction in a compound of the formula VI being bonded to halocarbonyl, for example chlorocarbonyl, or being in the form of the isocyanate group, and in the latter case it is possible to obtain only compounds of the formula I that carry a hydrogen atom at the nitrogen atom of the amide group formed by the reaction.

A reactive carboxylic acid derivative of a compound of the formula V is preferably reacted with a compound of the formula VI in which the amino or hydroxy group participating in the reaction is in free form.

Alternatively, a salt, for example a caesium salt, of a compound of the formula V in which q and r represent 1 and s represents 0 can be reacted with a compound of the formula VI in which X represents oxygen, v represents 1 and u and t each represents 0, the hydroxy group participating in the reaction being in reactive esterified form.

Finally, it is also possible to react a free acid of the formula V with a compound of the formula VI in which the group participating in the reaction is in activated form.

The acylation of a compound of the formula VI or a reactive derivative thereof with a compound of the formula V or a reactive acid derivative thereof can be carried out in a manner known per se, the reaction conditions depending especially on the type of acylating agent used, customarily in the presence of a suitable solvent or diluent or a mixture thereof, and, if necessary, in the presence of a condensation agent which, for example, when using an anhydride as the acylating agent, may also be an acid-binding agent, while cooling or heating, for example in a temperature range of from approximately $-30°$ C. to approximately $+150°$ C., in a closed reaction vessel and/or in the atmosphere of an inert gas, for example nitrogen.

The starting materials of the formulae V and VI are known or can be manufactured according to processes known per se, for example analogously to the processes described in this application.

Process d (phosphoric acid di-ester formation)

A reactive phosphoric acid derivative of an acid of the formula VII or VIII is, for example, a mono- or bis-anhydride with a strong acid, especially a mineral acid, such as especially a hydrohalic acid, such as chiefly hydrochloric acid. The second acid phosphoric acid group may be present as such or may be in the form of the anhydride as described above or in esterified form, there being preferred as esterifying radicals those which, after the reaction between the compounds VII and VIII, can be removed again regioselectively, for example the methyl ester group which can be removed, for example, by alkaline hydrolysis, or especially hydrogenolytically removable radicals, for example benzyl or phenyl ester radicals, it being possible to remove benzyl ester radicals, for example, in the presence of palladium catalysts, such as palladium-on-carbon, and phenyl ester groups, for example, in the presence of platinum or mixed platinum/palladium catalysts.

The formation of reactive phosphoric acid derivatives can also take place in situ in the presence of compounds that are capable of forming, with phosphoric acid or the mono-esters thereof, at least intermediately, reactive compounds of anhydride-like or enol ester-like character, for example in the presence of p-toluenesulphonyl chloride, cyanuric acid chloride, N-alkyl-5-phenylisoxazolium salts, ethoxyacetylene or, preferably, trichloroacetonitrile or, especially, a carbodiimide, such as chiefly dicyclohexyl carbodiimide. For example, a phosphoric acid mono-ester of the formula VII or VIII can be reacted with excess alcohol of the formula VII or VIII in the presence of a multiple of the molar quantity, for example five times the molar quantity, of dicyclohexyl carbodiimide in the presence or absence of a tertiary amine.

If, in a phosphoric acid mono-ester, both acid groups are in the form of the anhydride with a hydrohalic acid, it is possible to obtain first of all, in addition to the tri-ester, also phosphoric acid di-ester halides which can then be hydrolysed to form di-esters by using water, water-yielding agents or by heating with tertiary alcohols, such as tert.-butanol or tetrahydropyranol.

If a phosphoric acid mono-ester dihalide, for example a phosphoric acid mono-ester dichloride, is used as starting material, the reaction is preferably carried out in the presence of a tertiary amine, such as pyridine, lutidine or quinoline, an additional activation of the ester chloride being brought about by dimethylformamide.

A preferred embodiment of Process (d) is the reaction of a phosphoric acid mono-ester dichloride with the corresponding alcohol in the presence of a tertiary amine, followed by the hydrolysis of the phosphoric acid di-ester halide which is obtained first.

Process e (nucleophilic substitution by means of phospate)

Reactive esterified hydroxy groups are those mentioned in Process (a), preferably chlorides, bromides or iodides.

There are used as salts of compounds of the formula VII or VIII, in view of the intended nucleophilic substitution reaction, especially reactive salts, for example salts, such as silver salts, that, with the nucleophilic leaving group in the reactant, for example one of the halide ions mentioned above, is capable of forming a sparingly soluble precipitate, or salts with a large cation, for example caesium salts, in which the nucleophilic property of the phosphate ion is increased. In order to increase the nucleophilic property of the phosphate ion, the counter-ion can also be removed spatially, for example by the addition of complex-formers, such as Crown ethers, for example 18-Crown-6. When using 18-Crown-6, the reaction can be carried out with a potassium salt.

A preferred embodiment of Process (e) is the reaction of the silver salt of a phosphoric acid monoester of the formula VII or VIII in which one of the two acid groups is protected by a readily removable protecting group, for example one of those described in Process (d), for example in the form of the benzyl or phenyl ester, with a reactively esterified alcohol of the formula VII or VIII in which the OH group is substituted by chlorine, bromine or iodine. When the reaction is complete, the protecting group is removed, for example a benzyl or phenyl ester protecting group is removed by hydrogenation as described in Process (d).

Process f (esterification)

Reactive carboxylic acid derivatives of a compound of the formula IX are reactive esters, anhydrides or amides analogous to those mentioned in Process (a) or carboxylic acid salts.

Protecting groups are, for example, those mentioned above. A reactive derivative of a lower alkanol $R^8$—OH is, for example, one with a reactive esterified hydroxy group as described above, for example one of the compounds mentioned below.

The reaction is preferably carried out in such a manner that a carboxylic acid salt, for example a caesium salt, of a compound of the formula IX is reacted with the lower alkanol $R^8$—OH in which the hydroxy group is in reactive esterified form. Alternatively, a reactive carboxylic acid derivative of a compound of the formula IX can be esterified with the lower alkanol $R^8$—OH in which the OH group is in free form.

The esterification of free carboxy with the desired alcohol is preferably carried out in the presence of a suitable condensation agent. Customary condensation agents are, for example, carbodiimides, for example N,N'-diethyl, N,N'-dipropyl, N,N'-dicyclohexyl or N-ethyl-N'-(3-dimethylaminopropyl)carbodiimide, suitable carbonyl compounds, for example carbonyldiimidazole, or 1,2-oxazolium compounds, for example 2-ethyl-5-phenyl-1,2-oxazolium 3'-sulphonate and 2-tert.-butyl-5-methylisoxazolium perchlorate, or a suitable acylamino compound, for example 2-ethoxy-1-ethoxycarbonyl-1,2-dihydroquinoline. The condensation reaction is preferably carried out in an anhydrous reaction medium, preferably in the presence of a solvent or diluent, for example methylene chloride, dimethylformamide, acetonitrile or tetrahydrofuran, and, if necessary, while cooling or heating and/or in an inert gas atmosphere.

Furthermore, a free carboxylic acid of the formula IX can be reacted with a reactive derivative of a lower alkanol $R^8$—OH. Suitable derivatives of this type are, for example, corresponding diazo compounds, such as optionally substituted diazo-lower alkanes, for example diazomethane, diazoethane, diazo-n-butane or diphenyldiazomethane. These reagents are used in the presence of a suitable inert solvent, such as an aliphatic, cycloaliphatic or aromatic hydrocarbon, such as hexane, cyclohexane, benzene or toluene, a halogenated aliphatic hydrocarbon, for example methylene chloride, or an ether, such as a di-lower alkyl ether, for example diethyl ether, or a cyclic ether, for example tetrahydrofuran or dioxan, or a solvent mixture, and, depending on the diazo reagent, while cooling, at room temperature or while heating gently, also, if necessary, in a closed vessel and/or in an inert gas atmosphere, for example a nitrogen atmosphere.

Further suitable agents for esterifying a carboxy group in a compound of the formula IX are esters of corresponding alcohols, especially those with strong inorganic or organic acids, such as mineral acids, for example hydrohalic acids, such as hydrochloric, hydrobromic or hydriodic acid, also sulphuric acid, or halosulphuric acid, for example fluorosulphuric acid, or strong organic sulphonic acids, such as lower alkanesulphonic acids that are optionally substituted, for example by halogen, such as fluorine, or aromatic sulphonic acids, such as, for example, benzenesulphonic acids optionally substituted by lower alkyl, such as methyl, halogen, such as bromine, and/or by nitro, for example methanesulphonic, trifluoromethanesulphonic or p-toluenesulphonic acid. Such esters are, inter alia, lower alkyl halides, di-lower alkyl sulphates, such as dimethyl sulphate, also fluorosulphonic acid esters, such as fluorosulphonic acid lower alkyl esters, for example fluorosulphonic acid methyl ester, or optionally halo-substituted methanesulphonic acid lower alkyl esters, for example trifluoromethanesulphonic acid methyl ester. They are usually used in the presence of an inert solvent, such as an optionally halogenated, such as chlorinated, aliphatic, cycloaliphatic or aromatic hydrocarbon, for example methylene chloride, an ether, such as dioxan or tetrahydrofuran, or a mixture thereof. Suitable condensation agents are preferably used, such as alkali metal carbonates or bicarbonates, for example sodium or potassium carbonate or bicarbonate (usually together with a sulphate), or organic bases, such as tri-lower alkylamines that are customarily sterically hindered, for example N,N-diisopropyl-N-ethylamine (preferably together with halosulphonic acid lower alkyl esters or optionally halo-substituted methanesulphonic acid lower alkyl esters), the operation being carried out while cooling, at room temperature or while heating, for example at temperatures of from approximately $-20°$ C. to approximately $+50°$ C. and, if necessary, in a closed vessel and/or in an inert gas atmosphere, for example a nitrogen atmosphere.

Further agents for esterifying a carboxy group in a compound of the formula IX are corresponding tri-substituted oxonium salts (so-called Meerwein salts), or di-substituted carbenium or halonium salts in which the substituents are the etherifying radicals, for example tri-lower alkyloxonium salts, and also di-lower alkoxycarbenium salts or di-lower alkylhalonium salts, especially the corresponding salts with complex fluorine-containing acids, such as the corresponding tetrafluoroborates, hexafluorophosphates, hexafluoroantimonates, or hexachloroantimonates. Such reagents are, for example, trimethyloxonium or triethyloxonium hexafluoroantimonate, hexachloroantimonate, hexafluorophosphate or tetrafluoroborate, dimethoxycarbenium hexafluorophosphate or dimethylbromonium hexafluoroantimonate. These etherifying agents are preferably used in an inert solvent, such as an ether or a halogenated hydrocarbon, for example diethyl ether, tetrahydrofuran or methylene chloride, or a mixture thereof, if necessary in the presence of a base, such as an organic base, for example a preferably sterically hindered tri-lower alkylamine, for example N,N-diisopropyl-N-ethylamine, and while cooling, at room temperature or while heating gently, for example at from approximately −20° C. to approximately 50° C., if necessary in a closed vessel and/or in an inert gas atmosphere, for example a nitrogen atmosphere.

Process g (oxidation)

The compounds of the formula X are predominantly in the tautomeric form in which a proton is bonded directly to phosphorus. The oxidation can be carried out, for example, with aqueous potassium permanganate at temperatures of approximately 0° C. In aqueous medium there are also suitable as oxidising agents, inter alia, alkali iodates, periodates and hypochlorites, peracetic acid and N-chloro-4-methylbenzenesulphonic acid amide.

Process h ([furanose→pyranose] conversion)

There are used as protecting groups, for example, those mentioned above. Bivalent hydroxy-protecting groups are especially optionally substituted alkylidene or cycloalkylidene groups. Alkylidene is especially lower alkylidene, such as isopropylidene, and cycloalkylidene is especially cyclopentylidene or cyclohexylidene. There may be mentioned as substituents of the alkylidene radicals especially aromatic radicals, for example phenyl radicals.

The removal of the protecting groups mentioned in this application in general and the removal according to Process (h) in particular is carried out in a manner known per se by means of solvolysis, especially hydrolysis, alcoholysis or acidolysis, or in some cases alternatively by means of careful reduction, optionally in stages or simultaneously. Silyl protecting groups are advantageously removed with fluorides, for example tetraethylammonium flouride.

An especially preferred embodiment of Process (h) uses as starting materials compounds of the formula XI in which $R^{19}$ and $R^{20}$ together represent an optionally substituted alkylidene or cycloalkylidene radical and $R^{17}$ and $R^{18}$ together represent the group

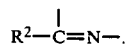

In that case the cleaving operation, which is especially suitable for the manufacture of N-benzoyl compounds of the formula I, is carried out with dilute acid, the best results being obtained at a pH of from 2 to 4, for example 3, as a one-pot reaction likewise in a manner known per se, for example with an acidic ion exchanger, especially one with sulphonic acid groups, such as Amberlite IR-120 (a styrene resin with strongly acidic sulpho groups) or Dowex 50 (polystyrenesulphonic acids) or a strong inorganic or organic acid, such as hydrochloric acid, hydrobromic acid, sulphuric acid or a sulphonic acid, for example methanesulphonic acid, or a phenylsulphonic acid optionally substituted in the aromatic ring, such as p-toluenesulphonic acid, or trifluoroacetic acid. If the operation is carried out in the presence of water, a free hydroxy group is obtained in the 1-position.

Process i (removal of protecting groups)

The removal of protecting groups from a compound of the formula I is carried out in a manner analogous to that of Process h.

Process j (hydrolysis of phosphoric acid di-ester halides)

In a compound of the formula XII, A represents halogen, such as bromine or iodine, but especially chlorine.

The hydrolysis is carried out with water or a water-yielding agent, preferably at elevated temperature, for example between 30° and 95° C.

The starting materials can be obtained, for example, by chlorinating the corresponding phosphorous acid di-esters, for example with elemental chlorine.

The starting materials required to carry out the above-mentioned processes are known or can be manufactured according to processes known per se, for example analogously to one of the processes described above.

The salts of the compounds of the formula I are generally formed as early as the working-up operation, for example during dialysis against a buffer solution having a pH of 7. They can be manufactured in a manner known per se. Thus, salts of compounds of the formula I may be formed, for example, by treatment with metal compounds, such as alkali metal salts of suitable organic carboxylic acids, for example the sodium salt of α-ethylcaproic acid, or with inorganic alkali metal or alkaline earth metal compounds, such as corresponding hydroxides, carbonates and bicarbonates, such as sodium or potassium hydroxide, carbonate or bicarbonate, or corresponding calcium compounds, or with ammonia or suitable organic amines, there being used preferably stoichiometric quantities or a slight excess of the salt-forming agent.

Mixtures of isomers can be separated in a manner known per se into the individual isomers, for example by fractional crystallisation, chromatography etc., and racemates may be separated, for example with the formation of derivatives with optically active compounds and separation of the diastereoisomeric mixtures obtainable in this manner, into the optically active antipodes.

The processes described above, including the processes for removing protecting groups and the additional process steps, are carried out in a manner known per se, for example in the presence or absence of solvents and diluents, if necessary in the presence of condensation agents or catalysts, at reduced or elevated temperature, for example in a temperature range of from approximately −20° C. to approximately 150° C., in a closed vessel and/or in an inert gas atmosphere, for example a nitrogen atmosphere.

Taking into consideration all the substituents present in the molecule, if necessary, for example if readily hydrolysable radicals are present, especially mild reaction conditions should be used, such as short reaction times, the use of mild acid or basic agents in low concentrations, stoichiometric quantity ratios and the selection of suitable catalysts, solvents, temperature and/or pressure conditions.

The invention relates also to those forms of the process in which a compound obtainable as intermediate at any stage of the process is used as starting material and the remaining process steps are carried out, or the process is discontinued at any stage, or a starting material is formed under the reaction conditions or is used in the form of a reactive derivative or salt. Preferably the starting materials used are those which according to the process result in the compounds described above as being especially valuable.

The invention relates also to pharmaceutical preparations which contain a pharmacologically active amount of the active ingredient, optionally together with pharmaceutically acceptable carriers which are suitable for enteral, for example oral or rectal, or parenteral administration, and may be inorganic or organic and solid or liquid. Thus, tablets or gelatin capsules are used which contain the active ingredient together with diluents, for example lactose, dextrose, sucrose, mannitol, sorbitol, cellulose and/or glycerine, and/or lubricants, for example silica, talc, stearic acid or salts thereof, such as magnesium or calcium stearate, and/or polyethylene glycol. Tablets may also contain binders, for example magnesium aluminium silicate, starches, such as corn, wheat or rice starch, gelatin, methylcellulose, sodium carboxymethylcellulose and/or polyvinylpyrrolidone, and, if desired, disintegrators, for example starches, agar, alginic acid or a salt thereof, such as sodium alginate, and/or effervescing mixtures, or adsorbents, colouring substances, flavourings and sweeteners. The pharmacologically active compounds of the present invention can also be used in the form of parenterally administrable preparations or infusion solutions. Such solutions are preferably isotonic aqueous solutions or suspensions, it being possible to manufacture these before use, for example in the case of lyophilised preparations which contain the active ingredient alone or together with a carrier, for example mannitol. The pharmaceutical preparations can be sterilised and/or contain adjuncts, for example preservatives, stabilisers, wetting agents and/or emulsifiers, solubilisers, salts for regulating the osmotic pressure and/or buffers. The present pharmaceutical preparations which may, if desired, contain further pharmacologically active ingredients, such as antibiotics, are manufactured in a manner known per se, for example by means of conventional mixing, granulating, confectioning, dissolving or lyophilising processes, and contain from approximately 0.001% to 99%, especially from approximately 0.01% to approximately 10%, especially between 0.1% and 5%, of the active ingredient(s), a concentration of active ingredient of less than 1% being suitable, especially for preparations to be administered topically.

Especially suitable for the prophylaxis and treatment of virus infections are the following forms of administration which are to be applied topically: creams, ointments or pastes having an active ingredient content of from 0.001% to 1%, especially from 0.01% to 0.1%, for example 0.05%, for example ointments for intranasal application or lipsticks, or aqueous solutions having an active ingredient content of from 0.001% to 1%, especially from 0.05% to 0.5%, for example 0.1%, preferably isotonic, sterile and physiologically tolerable solutions, for example eye drops, preferably in micro-containers for a single application, or sprays for application in the mouth and pharynx.

The pharmaceutical preparations described in the Examples are especially suitable.

Creams are oil-in-water emulsions that contain more than 50% of water. As oily base there are used especially fatty alcohols, for example lauryl, cetyl or stearyl alcohol, fatty acids, for example palmitic or stearic acid, liquid to solid waxes, for example isopropyl myristate, wool wax or beeswax, and/or hydrocarbons, for example petroleum jelly (petrolatum) or paraffin oil. As emulsifiers there come into consideration surface-active substances having predominantly hydrophilic properties, such as corresponding non-ionic emulsifiers, for example fatty acid esters of polyalcohols, or ethylene oxide adducts thereof, such as polyglycerine fatty acid esters or polyoxyethylene sorbitan fatty acid esters (Tweens), also polyoxyethylene fatty alcohol ethers or polyoxyethylene fatty acid esters, or corresponding ionic emulsifiers, such as alkali metal salts of fatty alcohol sulphates, for example sodium lauryl sulphate, sodium cetyl sulphate or sodium stearyl sulphate, which are customarily used in the presence of fatty alcohols, for example cetyl alcohol or stearyl alcohol. Additives to the aqueous phase are, inter alia, agents that reduce the drying out of the creams, for example polyalcohols, such as glycerine, sorbitol, propylene glycol and/or polyethylene glycols, also preservatives, perfumes etc.

Ointments are water-in-oil emulsions that contain up to 70%, but preferably from approximately 20% to approximately 50%, of water or aqueous phase. As fatty phase there come into consideration especially hydrocarbons, for example petroleum jelly, paraffin oil and/or hard paraffins, which, in order to improve the water-binding capacity, preferably contain suitable hydroxy compounds, such as fatty alcohols or esters thereof, for example cetyl alcohol or wool wax alcohols, or wool wax. Emulsifiers are corresponding lipophilic substances, such as sorbitan fatty acid esters (Spans), for example sorbitan oleate and/or sorbitan isostearate. Additives to the aqueous phase are, for example, humectants, such as polyalcohols, for example glycerine, propylene glycol, sorbitol and/or polyethylene glycol, and also preservatives, perfumes etc.

Fatty ointments are anhydrous and contain as base especially hydrocarbons, for example paraffin, petroleum jelly and/or liquid paraffins, and also natural or partially synthetic fats, for example coconut fatty acid triglyceride, or preferably hardened oils, for example hydrogenated ground nut oil or castor oil, and also fatty acid partial esters of glycerine, for example glycerine mono- and di-stearate, and also, for example, the fatty alcohols, which increase the water-absorbing capacity, emulsifiers and/or additives mentioned in connection with the ointments.

Pastes are creams and ointments containing powder ingredients that absorb secretions, such as metal oxides, for example titanium oxide or zinc oxide, also talc and/or aluminium silicates, the purpose of which is to bind any moisture or secretions present.

Foams are administered from pressurised containers, and are liquid oil-in-water emulsions in aerosol form, halogenated hydrocarbons, such as chlorofluoro-lower alkanes, for example dichlorodifluoromethane and dichlorotetrafluoroethane, being used as propellants. For the oily phase there are used, inter alia, hydrocarbons, for example paraffin oil, fatty alcohols, for example cetyl alcohol, fatty acid esters, for example isopropyl myristate, and/or other waxes. As emulsifiers there are used, inter alia, mixtures of those emulsifiers having predominantly hydrophilic properties, such as polyoxyethylene sorbitan fatty acid esters (Tweens), and those having predominantly lipophilic properties, such as sorbitan fatty acid esters (Spans). In addition, there may be used customary additives, such as preservatives etc.

Tinctures and solutions generally have an aqueous-ethanolic base to which there are added, inter alia, polyalcohols, for example glycerine, glycols, and/or polyethylene glycol, as humectants for reducing evaporation, and fat-restoring substances, such as fatty acid esters with lower polyethylene glycols, that is to say lipophilic substances that are soluble in the aqueous mixture, to replace the fatty substances that are taken from the skin by the ethanol, and, if necessary, other adjuncts and additives.

The pharmaceutical preparations for topical application are manufactured in a manner known per se, for example by dissolving or suspending the active ingredient in the base or, if necessary, in a part thereof. When processing the active ingredient in the form of a solution, it is usually dissolved in one of the two phases before emulsification; when processing the active ingredient in the form of a suspension, it is mixed with a part of the base after emulsification and then added to the remainder of the formulation.

The dosage of the active ingredient depends on various factors, such as mode of administration, species, the defensive condition of the organism and to a decisive extent on the type of disorder to be treated. Thus, the daily dose in the case of oral administration to warm-blooded animals weighing approximately 70 kg is between 0.0001 and 0.1 g, a dosage of less than 0.001 g being used especially to avoid the formation of metastases after removing a primary tumour.

To prevent virus infections a single dose of from approximately 0.5 mg to approximately 50 mg, preferably from 25 to 15 mg, for example 7 mg, of active ingredient is administered to a warm-blooded animal weighing approximately 70 kg, for example a human. If required at times of increased risk of infection, the administration of this dose is repeated at intervals of from 1 to 3 weeks, for example every 2 weeks.

The therapeutic dose for warm-blooded animals weighing approximately 70 kg is, in the case of a virus infection, between 1 mg and 50 mg, preferably between 5 and 20 mg, for example 10 mg, especially when administered orally. The dosage in the case of intranasal application is lower by up to a factor of 10. If required, the administration of the hexopyranose compounds of the formula I is repeated at intervals of a few days, for example from 1 to 3 days, until there is an improvement in the disease.

The following Examples illustrate the invention without limiting it in any way. The $R_f$ values are ascertained on silica gel thin layer plates manufactured by Merck. The ratio of the eluants in the eluant mixtures used is in parts by volume (v/v); temperatures are given in degrees Centigrade.

EXAMPLE 1

3.60 g (5.66 mmol) of N-acetylmuramyl-L-alanyl-D-glutamic acid $(C_\alpha)$-n-butyl ester (0.6 mol of H$_2$O) and 0.88 g (7.54 mmol) of N-hydroxysuccinimide are dissolved, while stirring, in 20 ml of a mixture of chloroform:methanol=4:1. 1.60 g (7.54 mmol) of solid dicyclohexyl carbodiimide are added, and a solution of 3.7 g (4.72 mmol) of the sodium salt of L-alanine-2-(1,2-dipalmitoyl-sn-glycero-3-hydroxyphosphoryloxy)ethylamide in 40 ml of chloroform are continuously added dropwise in the course of four hours at room temperature. After a further hour, the reaction solution is substantially concentrated in a rotary evaporator, 200 ml of dioxan are added and the whole is lyophilised.

The crude product is suspended in 100 ml of chloroform, 600 ml of ethyl acetate are added, and the whole is stirred in an ice bath for one hour. The insoluble dicyclohexyl urea is filtered off, and the filtrate is evaporated to dryness. The residue is purified over 700 g of silica gel 60, high purity (Merck, particle size: 70–230 mesh ASTM), on a column of 4.5 cm diameter and 80 cm length in the system chloroform:methanol:water=70:30:5. For this purpose, the material is dissolved in 14 ml of eluant and applied to the column. After a first run of two lots of 500 ml of mixture, 10 ml fractions are taken. The material contained in fractions 133 to 152 and 153 to 236 is in each case collected and subjected separately to diafiltration. Procedure in the case of the main fraction is as follows: the material is dissolved in 300 ml of double-distilled water, heated briefly to 40° C. and, after cooling, the insoluble dicyclohexyl urea is removed by centrifugation. The supernatant is placed in a dialysis cell (manufacturer: Amicon Corporation, Danvers, Mass., 01932 USA, model 402, ultrafilter PM 10/76 mm $\phi$, inert, non-ionic polymer based on polysulphone, average pore size 10 Å) and dialysed at 4 atmospheres gauge against 1.5 l of double-distilled water, 0.5 l of phosphate buffer/sodium chloride (each 0.1 molar, 1:1, pH=7) and 1.5 l of water until free from chloride. The internal dialysis product (70 ml) is sterile-filtered through a millipore filter (0.2$\mu$) and lyophilised. The sodium salt of N-acetylmuramyl-L-alanyl-D-glutamyl-$(C_\alpha)$-n-butyl ester-$(C_\gamma)$-L-alanine-2-(1,2-dipalmitoyl-sn-glycero-3-hydroxyphosphoryloxy)-ethylamide (3.4 mol of H$_2$O) is obtained in the form of a colourless powder; $[\alpha]_D^{20}=+14\pm1°$ (c=0.44, water), $R_f=0.37$ (chloroform:methanol:water=70:30:5) and $R_f=0.64$ (ethyl acetate:n-butanol:pyridine:acetic acid:water=42:21:21:6:10).

$C_{63}H_{115}O_{20}N_5PNa\cdot3.41H_2O$ (1381.63): Calc.: C: 54.77; H: 8.94; N: 5.07; P: 2.24; H$_2$O: 4.71. Found: C: 54.3; H: 9.1; N: 5.6; P: 2.3; H$_2$O: 4.7.

$C_{63}H_{115}O_{20}N_5PNa$ (1316.59): Calc.: Na: 1.75. Found: Na: 1.57.

The starting material is obtained as follows:

5.5 g (8.1 mmol) of 4,6-O-isopropylidene-N-acetylmuramyl-L-alanyl-D-glutamic acid $(C_\alpha)$-n-butyl-$(C_\gamma)$-benzyl ester, dissolved in 60 ml of 60% strength acetic acid, are left to stand overnight at room temperature. The faintly yellowish solution is concentrated at 30° C. in a rotary evaporator to approximately half its volume, 300 ml of dioxan are added and the whole is lyophilised. 0.8 g of a palladium-on-carbon catalyst (10% strength) is added to 4.8 g (~7.5 mmol) of the crude product, dissolved in 100 ml of a mixture of dimethoxyethane and water (9:1), and the mixture is treated with hydrogen for four hours. The catalyst is filtered off with suction, the filtrate is evaporated to dryness, and the residue is purified by chromatography twice over silica gel 60 (Merck, 1:200, 10 and 5 ml fractions) in the system chloroform:methanol:water=70:30:5. The fractions containing the product are combined and the solvent is evaporated. The crude product, partly in the form of the sodium salt (from silica gel), is dissolved in 40 ml of double-distilled water and poured over 50 ml of a well pre-purified, strongly acidic ion exchanger (DOWEX 50 W X8 50/100 mesh, H-form), and the column is subsequently washed with a total of 100 ml of double-distilled water. The eluate is filtered through a millipore filter (0.2$\mu$) and lyophilised. 3.7 g (69% of the theoretical amount) of N-acetylmuramyl-L-alanyl-D-glutamic acid $(C_\alpha)$-n-butyl ester are obtained in the form of a colourless powder containing 0.6 mol of water; $[\alpha]_D^{20}=+45\pm1°$ (c=1.142; methanol), $R_f=0.23$ (chloroform:methanol:water = 70:30:5) and $R_f$=0.40 (n-butanol:acetic acid:water = 75:7.5:21).

The starting material is obtained as follows:

4.4 g (11 mmol) of the sodium salt of N-acetyl-4,6-O-isopropylidenemuramic acid (2.5 mmol/g) are suspended in 60 ml of absolute dimethylformamide. While stirring well, there are added thereto, in succession, 4.4 g (11 mmol) of L-alanyl-D-glutamic acid ($C_{60}$)-n-butyl ester-($C_\gamma$)-benzyl ester hydrochloride, 2.53 g (22 mmol) of N-hydroxysuccinimide and, finally, 2.5 g (12.1 mmol) of dicyclohexyl carbodiimide, and the whole is stirred overnight at room temperature. In order to work up, the suspension is diluted with 100 ml of ethyl acetate and, after stirring for half an hour at 0° C., the undissolved material (dicyclohexyl urea, sodium chloride) is filtered off. The filtrate is concentrated by evaporation in a high vacuum at 30°, and the residue is taken up in 400 ml of ethyl acetate and extracted ten times with 50 ml of double-distilled water each time. After drying the organic phase and evaporating the solvent, there remains 5.6 g of N-acetyl-4,6-O-isopropylidene-L-alanyl-D-glutamic acid ($C_{60}$)-n-butyl ester-($C_\gamma$)-benzyl ester in the form of an amorphous powder; $[\alpha]_D^{20}$=+30°±1° (c=0.732; methanol), $R_f$=0.87 (chloroform:methanol:water=70:30:5) and $R_f$=0.83 (n-butanol:acetic acid:water=75:7.5:21).

The starting product is obtained as follows:

50 ml of 4.5N hydrochloric acid in absolute ethyl acetate are added dropwise to 5.6 g (12.1 mmol) of N-tert.-butoxycarbonyl-L-alanyl-D-glutamic acid ($C_\alpha$)-n-butyl ester-($C_\gamma$)-benzyl ester, dissolved in 20 ml of absolute ethyl acetate, while stirring well and with the exclusion of moisture, and the whole is left to stand at 0° for one hour. The yellowish solution is concentrated to approximately 20 ml at room temperature, 150 ml of dioxan are added and the whole is lyophilised. 4.75 g (97% of the theoretical amount) of L-alanyl-D-glutamic acid ($C_\alpha$)-n-butyl ester-($C_\gamma$)-benzyl ester hydrochloride are obtained in the form of a colourless oil; $[\alpha]_D^{20}$=+19±1° (c=0.313; methanol), $R_f$=0.58 (chloroform:methanol:water=70:30:5) and $R_f$=0.56 (ethyl acetate:n-butanol:pyridine:water=42:21:6:10).

The starting product is obtained as follows:

2.6 g (25.8 mmol) of N-methylmorpholine are added to 8.5 g (25.8 mmol) of D-glutamic acid ($C_\alpha$)-n-butyl ester-($C_\gamma$)-benzyl ester hydrochloride and 7.4 g (25.8 mmol) of N-tert.-butoxycarbonyl-L-alanine-N-hydroxysuccinimide ester, dissolved in 150 ml of absolute dimethylformamide, and the whole is left to stand at room temperature for 20 hours. The clear, yellow solution is concentrated by evaporation in a high vaccum at 30° C., the semi-solid residue is taken up in 500 ml of ethyl acetate and extracted seven times with 50 ml of water each time. The organic phase is dried with anhydrous sodium sulphate. The residue remaining after evaporation of the ethyl acetate is purified by chromatography over 600 g of silica gel 60 (Merck, particle size 70–230 mesh ASTM) in the system chloroform:methanol=98:2. The material contained in the fractions 36 to 82 is collected and dried. N-tert.-butoxycarbonyl-L-alanyl-D-glutamic acid ($C_\alpha$)-n-butyl ester-($C_\gamma$)-benzyl ester is obtained in the form of a colourless oil; $[\alpha]_D^{20}$=+7±1° (c=0.315; dimethylformamide), $R_f$=0.73 (chloroform:isopropanol:acetic acid=70:8:2) and $R_f$=0.75 (n-butanol:acetic acid:water=75:7.5:21).

The starting material is obtained as follows:

25 ml of 4N HCl in absolute ethyl acetate are added in the cold to 11.0 g (30 mmol) of N-tert.-butoxycarbonyl-D-glutamic acid ($C_\alpha$)-n-butyl ester-($C_\gamma$)-benzyl ester, dissolved in 25 ml of absolute ethyl acetate, while stirring and with the exclusion of moisture, and the whole is left to stand for one hour. The readily volatile constituents are evaporated off at 25° C., the oily residue is taken up in 150 ml of absolute diethyl ether and the latter is evaporated again (3 times). The oily residue is dried over soda-asbestos in a semi-vaccum. D-glutamic acid ($C_\alpha$)-n-butyl ester-($C_\gamma$)-benzyl ester hydrochloride is obtained; $[\alpha]_D^{20}$=−9±1° (c=0.646; methanol), $R_f$=0.82 (chloroform:methanol:water=70:30:5) and $R_f$=0.68 (ethyl acetate:n-butanol:pyridine:acetic acid:water=42:21:21:6:10).

The starting material is obtained as follows:

20.0 g (64.6 mmol) of N-tert.-butoxycarbonyl-D-glutamic acid ($C_\gamma$)-benzyl ester are dissolved in 750 ml of absolute tetrahydrofuran, 21.05 g (64.6 mmol) of caesium carbonate (Fluka, purum), dissolved in 80 ml of water, are added dropwise thereto, and the whole is evaporated to dryness under a water jet vacuum. The residue is taken up in 200 ml of absolute dimethylformamide, the solvent is evaporated and this operation is repeated. The crystalline residue obtained after drying in a high vacuum is dissolved in a liter of absolute dimethylformamide, and 13.3 g (97 mmol) of n-butyl bromide are added dropwise thereto while stirring. The suspension obtained after stirring for 18 hours at room temperature is filtered, the filtrate is concentrated to half its volume and, after the addition of one liter of ethyl acetate, speedily extracted ten times with 100 ml of water each time. The organic phase is dried over sodium sulphate and concentrated by evaporation. The oily residue is taken up in 100 ml of diethyl ether and induced to crystallise by the addition of 1800 ml of petroleum ether and leaving to stand at −10°. The crystal mass is filtered with suction, washed and dried. N-tert.-butoxycarbonyl-D-glutamic acid ($C_\alpha$)-n-butyl ester-($C_\gamma$)-benzyl ester is obtained in the form of colourless needles having a melting point of 70°–71°, $[\alpha]_D^{20}$=20±1° (c=1.149; methanol), $R_f$=0.77 (chloroform:isopropanol:acetic acid=30:82:2) and $R_f$=0.92 (ethyl acetate:n-butanol:pyridine:acetic acid:water=42:21:21:6:10), the preparation of which is already briefly described in P. Lefrancier and E. Lederer, *Fortschritte d. Chem. org. Naturst.* 40, 1–47, see page 13 (1980).

The L-alanine-2-(1,2-dipalmitoyl-sn-glycero-3-hydroxyphosphoryloxy)-ethylamide used as starting material is obtained as follows: 13.25 g (14.9 mmol) of N-tert.-butoxycarbonyl-L-alanine-2-(1,2-dipalmitoyl-sn-glycero-3-hydroxyphosphoryloxy)ethylamide are introduced, while stirring, into 170 ml of a mixture, cooled to 0° C., of trifluoroacetic acid and methylene chloride 1:3 (v/v), a clear solution being formed. After standing for 2½ hours at room temperature, the reaction solution is concentrated by evaporation in a rotary evaporator at 30° C. The semi-solid residue is treated repeatedly with 100 ml of methylene chloride each time to remove excess trifluoroacetic acid, the methylene chloride being evaporated in each case. After triturating the residue five times with 100 ml of absolute diethyl ether each time and decanting off the supernatant, a readily filtrable suspension is obtained. This is filtered with suction, and the solid material is washed first with diethyl ether, then twice with 100 ml of hot acetone each time, and dried under a water jet vacuum at 60°–70° C. 10.9 g of L-alanine-2-(1,2-dipalmitoyl-sn-glycero-3-hydroxyphosphoryloxy)-ethylamide are obtained in the form of colourless crystals with a melting point of 138°–147°, $[\alpha]_D^{20}=+30\pm1°$ (c=1; chloroform:methanol:water=70:30:5), $R_f=0.14$ (chloroform:methanol=7:3) and $R_f=0.40$ (chloroform:methanol:water=70:30:5).

The product obtained in this manner is converted into the sodium salt as follows:

3.82 g (5 mmol) of L-alanine-2-(1,2-dipalmitoyl-sn-glycero-3-hydroxyphosphoryloxy)-ethylamide are dissolved in 100 ml of a mixture of chloroform:methanol =7:3 by briefly heating to 35° C. The solution is cooled and 5 ml of 1N sodium hydroxide solution are cautiously added. The clear solution is concentrated to approximately ⅓ of the original volume and, after the addition of 200 ml of dioxan, lyophilised. The sodium salt of L-alanine-2-(1,2-dipalmitoyl-sn-glycero-3-hydroxyphosphoryloxy)-ethylamide is obtained in the form of a loose powder.

EXAMPLE 2

The compounds mentioned in Examples 3–10, and the following compounds, are obtained analogously to Example 1:

the sodium salt of N-acetylmuramyl-N-methyl-L-alanyl-D-glutamyl-($C_\alpha$)-ethyl ester-($C_\gamma$)-L-alanine-2-(1,-dipalmitoyl-sn-glycero-3-hydroxyphosphoryloxy)-ethylamide, the sodium salt of N-acetyldemethylmuramyl-L-alanyl-D-glutamyl-($C_\alpha$)-methyl ester-($C_\gamma$)-L-alanine-2-(1,2-dipalmitoyl-sn-glycero-3-hydroxyphosphoryloxy)-ethylamide, the sodium salt of N-acetylmuramyl-L-seryl-D-glutamyl-($C_\alpha$)-n-butyl ester-($C_\gamma$)-L-alanine-2-(1,2-dipalmitoyl-sn-glycero-3-hydroxyphosphoryloxy)-ethylamide, the sodium salt of N-acetylmuramyl-L-cysteinyl-D-glutamyl-($C_\alpha$)-n-butyl ester-($C_\gamma$)-L-alanine-2-(1,2-dipalmitoyl-sn-glycero-3-hydroxyphosphoryloxy)-ethylamide, the sodium salt of N-acetylmuramyl-L-methionyl-D-glutamyl-($C_\alpha$)-n-butyl ester-($C_\gamma$)-L-alanine-2-(1,2-dipalmitoyl-sn-glycero-3-hyroxyphosphoryloxy)-ethylamide, the sodium salt of N-acetylmuramyl-L-alanyl-D-glutamyl-($C_\alpha$)-n-butyl ester-($C_\gamma$)-L-alanine-2-(1,2-dimyristoyl-sn-glycero-3-hydroxyphosphoryloxy)-ethylamide, the sodium salt of N-acetylmuramyl-L-alanyl-D-glutamyl-($C_\alpha$)-n-butyl ester-($C_\gamma$)-L-alanine-2-(1,2-distearoyl-sn-glycero-3-hydroxyphosphoryloxy)-ethylamide, the sodium salt of N-acetylmuramyl-L-alanyl-D-glutamyl-($C_\alpha$)-n-butyl ester-($C_\gamma$)-L-alanine-2-(1,2-dioleoyl-sn-glycero-3-hydroxyphosphoryloxy)-ethylamide, the sodium salt of N-benzoylmuramyl-L-alanyl-D-glutamyl-($C_\alpha$)-n-butyl ester-($C_\gamma$)-L-alanine-2-(1,2-dipalmitoyl-sn-glycero-3-hydroxyphosphoryloxy)-ethylamide, the sodium salt of N-glycolylmuramyl-L-alanyl-D-glutamyl-($C_\alpha$)-n-butyl ester-($C_\gamma$)-L-alanine-2-(1,2-dipalmitoyl-sn-glycero-3-hydroxyphosphoryloxy)-ethylamide and the sodium salt of N-acetyl-1,4,6-O-triacetylmuramyl-L-alanyl-D-glutamyl-($C_\alpha$)-n-butylester-($C_\gamma$)-L-alanine-2-(1,2-dipalmitoyl-sn-glycero-3-hydroxyphosphoryloxy)-ethylamide.

EXAMPLE 3

Eye-drops

| Composition: | |
|---|---|
| the sodium salt of N—acetylmuramyl-L-α-aminobutyryl-D-glutamyl-($C_\alpha$)-n-butyl ester-($C_\gamma$)-L-alanine-2-(1,2-dipalmitoyl-sn-glycero-3-hydroxyphosphoryloxy)-ethyl-amide (compound II) | 0.10 mg |
| boric acid | 30.00 mg |
| sodium tetraborate.10H$_2$O | 0.10 mg |
| benzalkonium chloride | 0.20 mg |
| water for injection | to make up to 1.00 ml |

Preparation

The boric acid, sodium tetraborate and benzalkonium chloride are dissolved while stirring at room temperature under aseptic conditions in a portion of the above-mentioned quantity of water for injection. Compound II is then dissolved in the resulting solution, and water for injection is added to make up to the final volume of 1.0 ml.

The solution, or a portion of a multiple thereof, is filtered through a membrane filter and introduced into cleaned containers. Suitable containers are, for example: flexible plastics containers (5 ml or 10 ml) having a dropping attachment, glass containers (5 ml or 10 ml) having a glass or plastics dropping pipette and an elastomeric pipette filler, or plastic single-dose pipettes (contents 1–2 drops).

EXAMPLE 4

Non-aqueous single dose for nasal administration

| Composition: | |
|---|---|
| the sodium salt of N—propionyl-demethyl-muramyl-L-alanyl-D-glutamyl-($C_\alpha$)-n-butyl ester-($C_\gamma$)-L-alanine-2-(1,2-dipalmitoyl-sn-glycero-3-hydroxyphosphoryl-oxy)-ethylamide (compound III) | 0.03 mg |
| Miglyol 812 | to make up to 30.00 mg |

Preparation:

0.03 mg of compound III is dissolved under aseptic conditions in 29.97 mg of Miglyol 812.

This solution is introduced into a commercially available single-dose nasal applicator, for example an applicator according to U.S. Pat. No. 3,739,951, which is attached to an aerosol-container before use.

EXAMPLE 5

Nose drops

| Composition: | I | II |
|---|---|---|
| the sodium salt of N—acetylmuramyl-L-valyl-D-glutamyl-($C_\alpha$)-n-butyl ester-($C_\gamma$)-L-alanine-2-(1,2-dipalmitoyl-sn-glycero-3-hydroxyphosphoryloxy)-ethylamide (compound IV) | 0.15 mg | 0.10 mg |
| thiomersal | 0.02 mg | — |
| sodium monohydrogen phosphate.2H$_2$O | 0.30 mg | 0.30 mg |
| sodium dihydrogen phosphate.12H$_2$O | 10.10 mg | 10.10 mg |
| benzalkonium chloride | — | 0.10 mg |
| disodium salt of ethylenediamine-tetraacetic acid (EDTA) | 0.50 mg | 0.50 mg |
| sodium chloride | 3.70 mg | 4.50 mg |
| demineralised water | 988.30 mg | 987.60 mg |
| pH value: | 5.0 ± 0.3 | 5.0 ± 0.3 |

| Composition: | I | II |
|---|---|---|
| lowering of freezing point Δt | −0.51° C. | −0.56° C. |

Preparation:

While stirring at room temperature, the sodium dihydrogen phosphate, disodium monohydrogen phosphate, sodium chloride, thiomersal and the disodium salt of EDTA are dissolved in a portion of the above-mentioned quantity of demineralised water.

Compound IV is then dissolved in this solution and the remaining demineralised water is added.

The solution, or a portion or a multiple thereof, is filtered through a membrane filter and introduced into cleaned containers.

Suitable containers are, for example:
(a) glass or plastics containers (5 ml or 10 ml) having a glass or plastics pipette with an elastomeric pipette filler,
(b) compressible plastics bottles having a central tube and a plastics spraying head,
(c) single-dose plastics containers (contents 2–3 drops), or
(d) glass or plastics bottles that are provided with a standardised pumpable dosing spray made of plastics (no propellant).

EXAMPLE 6

Gel

| Composition: | |
|---|---|
| the sodium salt of N—acetylmuramyl-L-alanyl-D-glutamyl-($C_\alpha$)-n-butyl ester-($C_\gamma$)-L-alanine-2-(1,2-dilauroyl-sn-glycero-3-hydroxyphosphoryloxy)-ethylamide (compound V) | 0.01 g |
| glycerine 85% | 10.00 g |
| methyl paraben | 0.12 g |
| propyl paraben | 0.03 g |
| sodium carboxymethylcellulose (high viscosity) | 2.50 g |
| demineralised water | 87.34 g |

Preparation:

The methyl paraben and propyl paraben are dissolved in a portion of the hot demineralised water. The sodium carboxymethylcellulose is then incorporated into the resulting solution while stirring vigorously. While stirring, the glutinous product is allowed to swell. After cooling, the glycerine and a solution of the active ingredient (compound V) in the remaining water is then added to this product.

EXAMPLE 7

Cream

| Composition: | |
|---|---|
| the sodium salt of N—acetylmuramyl-L-alanyl-D-glutamyl-($C_\alpha$)-n-butyl ester-($C_\gamma$)-L-alanine-2-(1-palmitoyl-2-oleoyl-sn-glycero-3-hydroxyphosphoryloxy)-ethylamide (compound VI) | 0.10 g |
| sorbitan monostearate | 0.60 g |
| cetyl alcohol | 3.00 g |
| isopropyl palmitate | 2.00 g |
| methyl paraben | 0.12 g |
| paraffin oil, viscous | 10.00 g |
| PEG (20)-sorbitan monostearate | 4.40 g |
| propyl paraben | 0.03 g |
| 70% solution of crystalline sorbitol in demineralised water | 6.00 g |
| stearic acid | 9.00 g |
| demineralised water | 64.67 g |

Preparation:

The fatty phase, comprising sorbitan monostearate, cetyl alcohol, stearic acid, PEG (20)-sorbitan monostearate, isopropyl palmitate and paraffin oil, is melted. The methyl paraben and propyl paraben are then dissolved in a portion of the hot demineralised water. The sorbitol solution is added to the aqueous phase. While stirring, the aqueous phase is then added at approximately 75° C. to the fatty phase. The cream base is then allowed to cool while stirring. A solution of the active ingredient (compound VI) in the remaining water is then added to the cream base at approximately 40° C.

EXAMPLE 8

Nasal ointment

| Composition: | |
|---|---|
| the sodium salt of N—acetylmuramyl-L-alanyl-D-glutamyl-($C_\alpha$)-methyl ester-($C_\gamma$)-L-alanine-2-(1,2-dipalmitoyl-sn-glycero-3-hydroxyphosphoryloxy)-ethylamide (compound VII) | 0.03 g |
| paraffin oil, viscous | 20.00 g |
| white petroleum jelly | 30.00 g |
| wool fat, anhydrous | 40.00 g |
| demineralised water | 19.97 g |

Preparation:

The fatty phase, comprising paraffin oil, petroleum jelly and wool fat, is melted. The aqueous solution of the active ingredient is incorporated into the fatty phase at approximately 50° C.

EXAMPLE 9

Skin ointment

| Composition | |
|---|---|
| the sodium salt of N—propionyl-demethyl-muramyl-L-alanyl-D-glutamyl-($C_\alpha$)-n-butyl-ester-($C_\gamma$)-glycine-2-(1,2-dipalmitoyl-sn-glycero-3-hydroxyphosphoryloxy)-ethylamide (compound VIII) | 0.25 g |
| sorbitan sesquioleate | 10.00 g |
| white beeswax | 5.00 g |
| cetyl alcohol | 2.50 g |
| methyl paraben | 0.15 g |
| paraffin oil, viscous | 20.00 g |
| propyl paraben | 0.02 g |
| stearyl alcohol | 2.50 g |
| white petroleum jelly | 40.00 g |
| demineralised water | 19.58 g |

Preparation:

The fatty phase, comprising sorbitan sesquioleate, white beeswax, cetyl alcohol, paraffin oil, stearyl alcohol and white petroleum jelly, is melted. The methyl paraben and propyl paraben are then dissolved in the main quantity of the water at elevated temperature. The aqueous phase is incorporated into the fatty phase at approximately 80° C. A solution of the active ingredient (compound VIII) in the remaining water is added to the resulting ointment base at approximately 40° C.

EXAMPLE 10

Lipstick

| Composition: | |
|---|---|
| the sodium salt of N—acetylmuramyl-N—methyl-L-alanyl-D-glutamyl-($C_\alpha$)-n-butyl ester-($C_\gamma$)-L-alanine-2-(1,2-dipalmitoyl-sn-glycero-3-hydroxy phosphoryloxy)-ethylamide (compound IX) | 1.00 g |
| polyethylene glycol having an average molecular weight of 400 | 15.00 g |
| polyethylene glycol having an average molcular weight of 1000 | 83.00 g |
| polyethylene glycol having an average molecular weight of 4000 | 1.00 g |

Preparation

The active ingredient is finely dispersed in the molten polyethylene glycols. The viscous melt is poured into suitable lipstick cases and left to harden.

EXAMPLE 11

3.50 g (6.9 mmol) of N-acetylmuramyl-L-alanyl-D-glutamic acid ($C_\alpha$)-methyl ester and 1.20 g of N-hydroxy-succinimide are dissolved in 50 ml of a mixture of dimethylformamide, isopropanol and chloroform (1:3:6; v/v), 2.10 g (10.35 mmol) of dicyclohexyl carbodiimide are added, and the whole is stirred for one hour at room temperature with the exclusion of moisture. 50 ml of ethyl acetate are added to the suspension, the whole is stirred in an ice bath for 30 minutes, and the insoluble dicyclohexyl urea is filtered off. The filtrate is concentrated in a rotary evaporator to approximately 40 ml, the active ester is precipitated by the addition of 150 ml of absolute diethyl ether (twice), filtered off and dried, resulting in the ester with N-hydroxysuccinimide with $R_f=0.43$ (chloroform:methanol:water=70:30:5).

3.43 g (4.4 mmol) of L-alanine-2-(1,2-dipalmitoyl-sn-glycero-3-hydroxyphosphoryloxy)-ethylamide are suspended in 45 ml of chloroform and, at 40°, 0.86 ml (6.1 mmol) of triethylamine, dissolved in 5 ml of chloroform, are added dropwise in the course of five minutes resulting in a clear solution. There is added dropwise thereto in the course of five minutes, while stirring well and with the exclusion of moisture, a solution of the above-described active ester in 100 ml of a mixture of dimethylformamide, chloroform and dioxan (1:14:6; v/v). After stirring for 2½ hours at room temperature, the slightly turbid solution is evaporated to dryness in a rotary evaporator (30°). The crude product is purified over silica gel (60 high-purity, Merck, particle size: 70–230 mesh ASTM) in the system chloroform:methanol:water=70:30:5 (5 ml fractions). The TLC fractions containing the product are collected. The residue remaining after evaporating the solvent is dissolved in 250 ml of double-distilled water and purified analogously to Example 1 by diafiltration (AMICON stirrer cell, type 402, utrafilter PM 30/76 mm φ). The solution remaining in the cell is filtered through a millipore filter (0.2μ) and lyophilised. The sodium salt of N-acetyl-muramyl-L-alanyl-D-glutamyl-($C_\alpha$)-methyl ester-($C_\gamma$)-L-alanine-2-(1,2-dipalmitoyl-sn-glycero-3-hydroxy-phosphoryloxy)-ethylamide. 2.96 mol of $H_2O$ is obtained in the form of a colourless powder; $[\alpha]_D^{20} = +11\pm1°$ (c=0.285; 10% strength acetic acid), $R_f=0.25$ (chloroform:methanol:water=70:30:5) and $R_f=0.39$ (ethyl acetate:n-butanol:pyridine:acetic acid:water=42:21:21:6:10).

The starting compound is obtained as follows:

7.7 g (21.2 mmol) of L-alanyl-D-glutamic acid ($C_\alpha$)-methyl ester-($C_\gamma$)-benzyl ester hydrochloride and 8.96 g (23.3 mmol) of the sodium salt of N-acetyl-4,6-O-isopropylidenemuramic acid are linked analogously to Example 1 in accordance with the dicyclohexyl carbodiimide/N-hydroxysuccinimide method. The crude product, without being further purified, is cleaved in 100 ml of 60% strength acetic acid. After stirring for 5½ hours at room temperature, the solution is substantially concentrated, water is added, the solution is again concentrated and, after the addition of 100 ml of dioxan, lyophilised. The residue is purified (twice) over 600 g of silica gel 60 in the system chloroform:methanol:water=70:30:5 (7 ml fractions).

The fractions containing the desired material are combined and the solvent is evaporated. There remains N-acetylmuramyl-L-alanyl-D-glutamic acid ($C_\alpha$)-methyl ester ($C_\gamma$)-benzyl ester in the form of a colourless foam with $R_f=0.63$ (chloroform:methanol:water=70:30:5).

6.0 g (10 mmol) of N-acetylmuramyl-L-alanyl-D-glutamic acid ($C_\alpha$)-methyl ester-($C_\gamma$)-benzyl ester, dissolved in a mixture of 1,2-dimethoxyethane and water 95:5 (v/v), are hydrogenated for 1½ hours at normal pressure in the presence of 0.6 g of a palladium-on-carbon catalyst (10% strength). The catalyst is filtered off and the filtrate is concentrated by evaporation under reduced pressure at room temperature. The residue is purified as above over 400 g of silica gel 60 in the system chloroform:methanol:water=70:30:5 (10 ml fractions). The fractions containing the product are combined and the solvent is evaporated. The residue that remains, partly in the form of the Na-salt, is demineralised analogously to the manner described in Example 1 using 50 ml of DOWEX 50 W X8 (50/100 mesh, H-form, strongly acidic cation exchanger). The filtrate is filtered through a millipore filter (0.45μ) and lyophilised. N-acetylmuramyl-L-alanyl-D-glutamic acid ($C_\alpha$)-methyl ester (1.27 mol of $H_2O$) is obtained in the form of a colourless powder; $[\alpha]_D^{20}= +47\pm1°$ (c=1.249; methanol), $R_f=0.08$ (chloroform:methanol:water=70:30:5), $R_f=0.30$ (acetonitrile:water =3:1) and $R_f=0.43$ (ethyl acetate:acetic acid:water:methanol=67:10:23:12).

EXAMPLE 12

9.4 g (11.1 mmol) of N-acetylmuramyl-L-alanyl-D-glutamic acid ($C_\alpha$)-tert.-butyl ester are converted into the active ester analogously to Example 11 and then, as described therein, linked with 6.48 g (8.2 mmol) of L-alanine-2-(1,2-dipalmitoyl-sn-glycero-3-hydroxyphosphoryloxy)-ethylamide in the presence of triethylamine. The crude product is suspended in 250 ml of double-distilled water and heated briefly to 37° C. The suspension is stirred for 15 minutes in an ice bath, the insoluble dicyclohexyl urea is filtered off and the filtrate is subjected to the diafiltration described in Example 1 (AMICON stirrer cell 402, ultrafilter PM 30/76 mm φ). The solution remaining in the cell (120 ml) is lyophilised and the product is chromatographed in customary manner over 550 g of silica gel 60. The desired material is collected, taken up in 200 ml of double-distilled water (pH =7), sterile-filtered (0.45μ) and lyophilised. The sodium salt of N-acetylmuramyl-L-alanyl-D-glutamyl-($C_\alpha$)-tert.-butyl ester-($C_\gamma$)-L-alanine-2-(1,2-dipalmitoyl-sn-glycero-3-hydroxyphosphoryloxy)-ethylamide is obtained in the form of a colourless powder containing 3.4 mol of water; $[\alpha]_D^{20}= +14\pm1°$ (c=0.817; 10% strength acetic acid), $R_f=0.29$ (chloroform:methanol:-water=70:30:5) and $R_f=0.53$ (ethyl acetate:n-butanol:-pyridine:acetic acid:water=42:21:21:6:10).

The muramyl dipeptide derivative required as starting material is obtained analogously to Example 1 by linking the sodium salt of N-acetyl-4,6-O-isopropylidenemuramic acid and L-alanyl-D-glutamic acid $(C_\alpha)$-tert.-butyl ester-$(C_\gamma)$-benzyl ester in accordance with the dicyclohexyl carbodiimide/N-hydroxysuccinimide method. After removal of the isopropylidene radical using 60% strength acetic acid, and after removal of the benzyl radical by catalytic hydrogenation analogously to Example 1, N-acetylmuramyl-L-alanyl-D-glutamic acid $(C_\alpha)$-tert.-butyl ester is obtained in the form of a colourless powder; $[\alpha]_D^{20}=+44\pm1°$ (c=1.004; methanol), $R_f=0.20$ (chloroform:methanol:-water=70:30:5) and $R_f=0.41$ (acetonitrile:water=3:1).

The dipeptide derivative required as starting material is obtained as follows:

38.3 g (63.5 mmol) of N-[2-(4-biphenylyl)-propoxycarbonyl]-L-alanyl-D-glutamic acid $(C_\alpha)$-tert.-butyl ester $(C_\gamma)$-benzyl ester are dissolved in 700 ml of a mixture of trifluoroethanol and water=9:1 (v/v) and, by the dropwise addition of 1.23N hydrochloric acid in the same solvent mixture (1 part by volume of concentrated hydrochloric acid and 9 parts by volume of trifluoroethanol) the "pH" value is reduced to 1.5 ($2\frac{1}{2}$ hours, consumption 51.66 ml, i.e. 81% of the theoretical amount). The faintly yellowish solution is concentrated in a rotary evaporator under a water jet vacuum at 30° to barely 100 ml, 200 ml of dioxan are added and the whole is freeze-dried. The semi-solid residue is taken up in 30 ml of absolute diethyl ether and precipitated at from 0° to 5°, while stirring, by the addition of 150 ml of petroleum ether. The mixture is allowed to stand in the cold ($-20°$), is decanted and the same procedure is repeated a further twice. The oily residue is finally taken up in 100 ml of tert.-butanol, lyophilised and the residue is dried in a high vacuum over soda-asbestos (Merck).

L-alanyl-D-glutamic acid $(C_\alpha)$-tert.-butyl ester-$(C_\gamma)$-benzyl ester hydrochloride is obtained in the form of a strongly hygroscopic powder; $[\alpha]_D^{20}=+7\pm1°$ (c=1.630; chloroform), $R_f=0.60$ (chloroform:methanol:water=70:30:5) and $R_f=0.45$ (n-butanol:acetic acid:water=10:1:2.8).

The protected compound is obtained as follows:

22 ml (0.24 mol) of N-methylmorpholine, and then 59.11 g (0.24 mol) of 2-ethoxy-N-ethoxycarbonyl-1,2-dihydroquinoline (EEDQ) are added, while stirring, to a solution, cooled to 0°, of 65.96 g (0.2 mol) of D-glutamic acid $(C_\alpha)$-tert.-butyl ester-$(C_\gamma)$-benzyl ester hydrochloride and 65.47 g (0.2 mol) of N-[2-(4-biphenylyl)-propoxycarbonyl]-L-alanine in 650 ml of absolute dimethylformamide. After stirring for ten hours at room temperature, the yellow solution is concentrated by evaporation at 30° in a rotary evaporator. The residue is taken up in 1 liter of ethyl acetate, extracted five times with 200 ml of water each time, the aqueous phase is re-extracted with 0.5 l of ethyl acetate and the combined organic phases are dried. The crude product (150 g) obtained after evaporation of the solvent is purified by repeated chromatography over silica gel 60 (1:20) with ethyl acetate. N-[2-(4-biphenylyl)-propoxycarbonyl]-L-alanyl-D-glutamic acid $(C_\alpha)$-tert.-butyl ester-$(C_\gamma)$-benzyl ester is obtained in the form of a colourless oil; $[\alpha]_D^{20}=-14\pm1°$ (c=1.625; ethyl acetate), $R_f=0.73$ (chloroform:isopropanol:acetic acid=70:8:2) and $R_f=0.51$ (toluene:ethyl acetate=1:1).

The D-glutamic acid $(C_\alpha)$-tert.-butyl ester-$(C_\gamma)$-benzyl ester hydrochloride used as starting material is obtained, analogously to the L-derivative described in the literature [R. Roeske, J. Org. Chem. 28, 1251 (1963)] by the reaction of D-glutamic acid $(C_\gamma)$-benzyl ester with isobutene in a mixture of 1,4-dioxan and sulphuric acid, in the form of colourless needles having a melting point of 108°-109°; $[\alpha]_D^{20}=-16\pm1°$ (c=1.235; ethanol), $R_f=0.84$ (chloroform:methanol:water=70:30:5) and $R_f=0.64$ (ethyl acetate:n-butanol:pyridine:acetic acid:-water=42:21:21:6:10).

EXAMPLE 13

14.52 ml (7.26 mmol) of a 0.5 molar triethylamine solution in a mixture of chloroform:isopropanol:-water=70:30:2 are added dropwise at 15° in the course of 10 minutes, while stirring, to a solution of 4.62 g (6.05 mmol) of L-alanine-2-(1,2-dipalmitoyl-sn-glycero-3-hydroxyphosphoryloxy)-ethylamide in 100 ml of a mixture of chloroform:isopropanol:water=70:30:2.

Then, in 20 minutes, 6.0 g (7.26 mmol) of N-propionyl-demethylmuramyl-L-alanyl-D-glutamic acid $(C_\alpha)$-methyl ester-$(C_\gamma)$-N-hydroxysuccinimide ester, still containing some dicyclohexyl urea, is added in solid form in 4 portions each of 1.5 g, the solution becoming noticeably more turbid.

After stirring for about 15 minutes at 15°, cooling is withdrawn and stirring is continued for $2\frac{1}{2}$ hours at room temperature.

The resulting turbid reaction solution is then concentrated by evaporation in vacuo at 30°. The crude product (10.75 g) is subsequently suspended in 170 ml of bidistilled water (pH 5.5), the suspension is adjusted to pH 6.0 by the addition of 0.3 ml of triethylamine, insoluble material (dicyclohexyl urea) is removed by filtration, and the filtrate is lyophilised in a high vacuum.

The resulting lyophilisate is dissolved in 300 ml of bidistilled water and the solution is concentrated in an AMICON dialysis cell (model 402, ultrafilter PM 10/76 mm $\phi$) at 3 atmospheres gauge (atmospheric excess pressure) to 75 ml, then filtered until free from chloride using 250 ml of phosphate buffer:sodium chloride (each 0.1 molar, 1:1, pH 7) and 1750 ml of bidistilled water. The solution remaining in the cell (approximately 75 ml) is then filtered in succession through two millipore filters (NALGENE S, 0.45$\mu$ and 0.2$\mu$), and the resulting clear, colourless solution is lyophilised in a high vacuum.

7.36 g of still impure sodium salt of N-propionyl-demethylmuramyl-L-alanyl-D-glutamyl-$(C_\alpha)$-methyl ester-$(C_\gamma)$-L-alanine-2-(1,2-dipalmitoyl-sn-glycero-3-hyroxyphosphoryloxy)-ethylamide are obtained in the form of a colourless powder, which is further purified by CRAIG-distribution with carbon tetrachloride:chloroform:methanol:0.5% strength sodium chloride solution=7:17:18:6. After 547 stages, the desired product is found in fractions 160-220, K=0.58. The fractions containing the product are combined and concentrated to dryness by evaporation in a high vacuum without heating (cooling). A colourless powder is obtained which still contains sodium chloride. In order to remove the latter, the product is dissolved in 600 ml of bidistilled water and filtered until free from chloride in an AMICON dialysis cell (model 402, ultrafilter PM 30/76 mm $\phi$) at 3 atmospheres gauge first to an internal volume of approximately 50 ml, then with a total of 1750 ml of bidistilled water.

The solution remaining in the cell (approximately 50 ml) is then sterile-filtered in succession through two millipore filters (NALGENE S, 0.45μ and 0.2μ), and lyophilised in a high vacuum.

The sodium salt of N-propionyl-demethylmuramyl-L-alanyl-D-glutamyl-($C_\alpha$)-methyl ester-($C_\gamma$)-L-alanine-2-(1,2-dipalmitoyl-sn-glycero-3-hydroxyphosphoryloxy)-ethylamide is obtained in the form of a colourless powder containing 1.90 mol of water; $[\alpha]_D^{20}=+3.7\pm0.1°$ (c=0.672; chloroform), $[\alpha]_D^{20}=+1.7\pm0.1°$ (c=1.044; water), $R_f=0.42$ (chloroform:methanol:water=70:30:5) and $R_f=0.62$ (ethyl acetate:n-butanol:pyridine:acetic acid:water=42:21:21:6:10).

The starting material is obtained as follows:

5.12 g (10.1 mmol) of N-propionyl-demethylmuramyl-L-alanyl-D-glutamic acid α-methyl ester are taken up in 100 ml of a mixture of chloroform:isopropanol=7:3 and completely dissolved by the addition of 10 ml of dimethylformamide.

There are added to this solution 2.68 g (13 mmol) of dicyclohexyl carbodiimide and 1.50 g (13 mmol) of N-hydroxysuccinimide, and the resulting clear, colourless solution is stirred for 1½ hours at room temperature and then left to stand for 17 hours at 4°.

400 ml of diethyl ether are added to the resulting suspension and stirring is then carried out for a further hour at room temperature.

The product of crystallisation is then filtered with suction, subsequently washed with diethyl ether and dried in vacuo over phosphorus pentoxide.

Crude N-propionyl-demethylmuramyl-L-alanyl-D-glutamic acid ($C_\alpha$)-methyl ester-($C_\gamma$)-N-hydroxysuccinimide ester is obtained in the form of colourless crystals, which still in fact contain some dicyclohexyl urea and are used without being further purified; $R_f=0.46$ (chloroform:methanol=5:1) and $R_f=0.72$ (chloroform:methanol=7.3).

The starting material is obtained as follows:

A solution of 13.0 g (21.75 mmol) of N-propionyl-demethylmuramyl-L-alanyl-D-glutamic acid ($C_\alpha$)-methyl ester-($C_\gamma$)-benzyl ester in 250 ml of a mixture of dimethoxyethane:water =20:1 is hydrogenated for 1 hour at room temperature and normal pressure with 2.5 g of 10% strength palladium-on-carbon as catalyst.

Subsequently the catalyst is filtered off, the filtrate is concentrated to dryness by evaporation in vacuo, and the resulting residue is three times taken up in 50 ml of water and concentrated by evaporation again.

The residue is dissolved again in about 100 ml of bidistilled water, and this solution is filtered through a millipore filter (NALGENE S, 0.2μ), and lyophilised in a high vacuum.

N-propionyl-demethylmuramyl-L-alanyl-D-glutamic acid α-methyl ester (0.68 mol of water) is obtained in the form of a colourless lyophilisate; $[\alpha]_D^{20}=+14.9\pm1°$ (c=1.067; methanol), $R_f=0.78$ (chloroform:methanol:water=70:30:5) and $R_f=0.57$ (ethyl acetate:n-butanol:pyridine:acetic acid:water=42:21:21:6:10).

The starting material is obtained as follows:

A solution of 20.7 g (32.46 mmol) of 4,6-O-isopropylidene-N-propionyl-demethylmuramyl-L-alanyl-D-glutamic acid ($C_\alpha$)-methyl ester-($C_\gamma$)-benzyl ester in 400 ml of 60% strength acetic acid is stirred at room temperature for 21 hours, then concentrated by evaporation in vacuo at 30°, and three times in succession, 100 ml of water are added to the resulting residue which is concentrated by evaporation again. The crude product is then purified by column chromatography over 1000 g of silica gel (60 high-purity, Merck, 0.063–0.200 mm) in the system methylene chloride:methanol=85:15 (15 ml fractions). Fractions 207–290 are combined and concentrated by evaporation in vacuo at 30°.

N-propionyl-demethylmuramyl-L-alanyl-D-glutamic acid ($C_\alpha$)-methyl ester-($C_\gamma$)-benzyl ester, which contains 0.24 mol of water, is obtained, $[\alpha]_D^{20}=+16.1\pm0.1°$ (c=1.463; methanol), $R_f=0.24$ (chloroform:methanol=9.1), $R_f=0.55$ (chloroform:methanol=5:1) and $R_f=0.94$ (chloroform:methanol:water=70:30:5).

The starting material is obtained as follows:

0.6 g (46.5 mmol) of dicyclohexyl carbodiimide, 5.35 g (46.5 mmol) of N-hydroxysuccinimide and 12.8 g (35.77 mmol) of L-alanyl-D-glutamic acid ($C_\alpha$)-methyl ester-($C_\gamma$)-benzyl ester hydrochloride are added at room temperature, while stirring, to a suspension of 13.2 g (35.77 mmol) of the sodium salt of 4,6-O-isopropylidene-N-propionyl-demethylmuramic acid in 200 ml of dimethylformamide and the whole is stirred for 21 hours at room temperature.

200 ml of ethyl acetate are added to the resulting white suspension, the whole is stirred for 1 hour at 0°, the crystallisate (dicyclohexyl urea) is filtered off with suction, subsequently washed with ice-cold ethyl acetate and the filtrate is concentrated by evaporation in vacuo at 30°.

The resulting residue is taken up in 300 ml of ethyl acetate and washed twice, successively, with in each case 50 ml of 2N citric acid, water, 10% sodium hydrogen carbonate solution and water.

The ethyl acetate phases are combined, dried over sodium sulphate, filtered and concentrated by evaporation in vacuo.

4,6-O-isopropylidene-N-propionyl-demethylmuramyl-L-alanyl-D-glutamic acid ($C_\alpha$)-methyl ester-($C_\gamma$)-benzyl ester is obtained; $R_f=0.65$ (chloroform:methanol=9:1) and $R_f=0.86$ (chloroform:methanol=5:1).

The two starting products are obtained as follows:

100 ml of approximately 5N hydrochloric acid in absolute ethyl acetate are added at 0° to a solution of 20.3 g (48.0 mmol) of N-tert.-butoxycarbonyl-L-alanyl-D-glutamic acid ($C_\alpha$)-methyl ester-($C_\gamma$)-benzyl ester [P. Lefrancier, M. Derrien, I. Lederman, F. Nief, J. Choay and E. Lederer, Int. J. Peptide Protein Res. 11, 289–296 (1978)] in 100 ml of absolute ethyl acetate and the whole is stirred for 2 hours at 0°. The yellowish solution is then concentrated by evaporation in vacuo, and the resulting residue is twice taken up in 100 ml of absolute ethyl acetate and concentrated by evaporation again. After digesting twice with 100 ml of absolute diethyl ether each time, the residue is dried in a high vacuum and L-alanyl-D-glutamic acid ($C_\alpha$)-methyl ester-($C_\gamma$)-benzyl ester hydrochloride containing 0.31 mol of water is obtained; $[\alpha]_D^{20}=+18.6\pm0.1°$ (c=0.043; methanol), $R_f=0.72$ (chloroform:methanol:water=70:30:5), $R_f=0.44$ (chloroform:methanol=5:1) and $R_f=0.31$ (chloroform:methanol=9:1).

A solution of 34.4 g (73.8 mmol, 2.14 mmol/g, still contains sodium chloride) of the sodium salt of 1α-O-benzyl:4,6-O-isopropylidene-N-propionyl-demethylmuramic acid in 340 ml of water is hydrogenated for 23 hours at room temperature and normal pressure, at a constant pH value of 7.1, with 6.0 g of 10% strength palladium-on-carbon as catalyst.

The catalyst is then filtered off, the filtrate is concentrated by evaporation in vacuo at pH 7.1 and 30°, and the resulting residue is dried over phosphorus pentoxide in a high vacuum.

The sodium salt of 4,6-O-isopropylidene-N-propionyl-demethylmuramic acid is obtained in the form of a colourless powder; $R_f=0.50$ (chloroform:methanol:water=70:30:5) and $R_f=0.66$ (acetonitrile:water=3:1).

The starting material is obtained as follows:

24.4 ml (48.7 mmol) of 2N sodium hydroxide solution are added to a solution of 14.3 g (32.7 mmol) of 1α-O-benzyl-4,6-O-isopropylidene-N-propionyl-demethylmuramic acid methyl ester in 130 ml of methanol and the whole is stirred at room temperature for 1½ hours.

Then, the resulting clear, faintly yellow solution is adjusted to pH 7.0 with 1N hydrochloric acid and concentrated by evaporation in vacuo at 30°. After drying over phosphorus pentoxide, the sodium salt of 1α-O-benzyl-4,6-O-isopropylidene-N-propionyl-demethylmuramic acid is obtained in the form of colourless crystals; $R_f=0.67$ (chloroform:methanol:water=70:30:5) and $R_f=0.74$ (acetonitrile:water=3:1)

The starting product is obtained as follows:

A solution of 31.3 g (85.65 mmol) of 1α-O-benzyl-2-deoxy-4,6-O-isopropylidene-2-propionamido-6β-D-glucopyranoside in 200 ml of absolute tetrahydrofuran is added dropwise at 5° in the course of 5 minutes, under nitrogen and while stirring, to a suspension of 6.75 g (224.7 mmol) of sodium hydride in 120 ml of absolute tetrahydrofuran, the temperature rising to 20°.

The resulting suspension is stirred for a further two hours at 40°, then cooled to 0° and added dropwise in the course of 30 minutes to a solution, cooled to −15°, of 20.7 g (135.77 mmol) of bromoacetic acid methyl ester in 95 ml of absolute tetrahydrofuran, under nitrogen while stirring.

The resulting suspension is stirred for a further 3 hours at 0°–5°, then 20 ml of methanol and 20 ml of tetrahydrofuran are added thereto. The pH is adjusted to 6 with 4.5 ml of glacial acetic acid, and the mixture is concentrated by evaporation in vacuo at 30°.

The residue is then dissolved in 200 ml of methylene chloride and the resulting solution is washed three times with 125 ml of water each time. The methylene chloride phases are combined, dried over sodium sulphate, filtered and concentrated by evaporation in vacuo at 30°.

A crude product is obtained in the form of faintly yellow crystals, which are purified by colomn chromatography over 500 g of neutral aluminium oxide (Woelm N, Super 1) with ethyl acetate as eluant (10 ml fractions). Fractions 14–36 are combined and concentrated by evaporation in vacuo.

1α-O-benzyl-4,6-O-isopropylidene-N-propionyl-demethylmuramic acid methyl ester is obtained in the form of colourless crystals having a melting point of 121°–123° (from diethyl ether:petroleum ether=1:2); $[\alpha]_D^{20}=+146.9\pm0.1°$ (c=0.849; chloroform) and $R_f=0.67$ (chloroform:methanol=9:1).

EXAMPLE 14

Analogously to example 13 there is obtained, from 5.525 g (6.43 mmol) of crude (still contains some dicyclohexyl urea) N-propionyl:demethylmuramyl-L-alanyl-D-glutamic acid ($C_\alpha$)-tert.-butyl ester-($C_\gamma$)-N-hydroxysuccinimide ester and 3.78 g (4.95 mmol) of L-alanine-2-(1,2-dipalmitoyl-sn-glycero-3-hydroxyphosphoryloxy)-ethylamide, the sodium salt of N-propionyl-demethylmuramyl-L-alanyl-D-glutamyl-($C_\alpha$)-tert.butyl ester-($C_\gamma$)-L-alanine-2-(1,2-dipalmitoyl-sn-glycero-3-hydroxyphosphoryloxy)-ethylamide in the form of a colourless powder containing 2.64 mol of water; $[\alpha]_D^{20}=+2.5\pm0.1°$ (c=0.649; water), $[\alpha]_D^{20}=5.8\pm0.1°$ (c=0.694; chloroform) and $R_f=0.60$ (chloroform:methanol:water=70:30:5).

The starting material is obtained as follows:

Analogously to Example 13 there is obtained, from 3.44 g (6.15 mmol) of N-propionyl-demethylmuramyl-L-alanyl-D-glutamic acid α-tert.-butyl ester, 1.68 g (8.14 mmol) of dicyclohexyl carbodiimide and 0.94 g (8.14 mmol) of N-hydroxysuccinimide, crude N-propionyl-demethylmuramyl-L-alanyl-D-glutamic acid ($C_\alpha$)-tert.-butyl ester-($C_\gamma$)-N-hydrxysuccinimide ester in the form of colourless crystals, which in fact will contain some dicyclohexyl urea and are used without being further purified: $R_f=0.61$ (chloroform:methanol:water=70:30:5).

The starting material is obtained as follows:

A solution of 5.1 g (7 mmol) of 1α-O-benzyl-N-propionyl:demethylmuramyl-L-alanyl-D-glutamic acid ($C_\alpha$)-tert.-butyl ester-($C_\gamma$)-benzyl ester in 100 ml of a mixture of dimethoxyethane:water=9.1 is hydrogenated for 20 hours at room temperature and normal pressure with 1.5 g of 5% strength palladium-on-carbon (E 101N, Degussa) as catalyst. After 20 hours the catalyst is filtered off and hydrogenation is then carried out again for a further 26 hours, as above, with 1.5 g of fresh catalyst. The catalyst is then filtered off again and the filtrate is concentrated to dryness by evaporation in vacuo at 30°.

The resulting residue is dissolved in a mixture of 100 ml of methylene chloride and 5 ml of isopropanol, 500 ml of a mixture of diethyl ether:petroleum ether=3:2 are added to the solution, and the whole is stirred for a further hour at room temperature.

The precipitated product is then filtered off with suction and subsequently washed with diethyl ester. N-propionyl-demethylmuramyl-L-alanyl-D-glutamic acid α-tert.-butyl ester is obtained in the form of a colourless powder containing 0.52 mol of water; $[\alpha]_D^{20}=+20.2\pm0.1°$ (c=0.902; water), $R_f=0.32$ (chloroform:methanol:water=70:30:5) and $R_f=0.54$ (acetonitrile:water=3:1).

The starting material is obtained as follows:

In an analogous manner to that described in Example 13 there is obtained, from 7.3 g (9.5 mmol) of 1α-O-benzyl-4,6-O-isopropylidene-N-propionyl-demethylmuramyl-L-alanyl-D-glutamic acid ($C_\alpha$)-tert.-butyl ester-($C_\gamma$)-benzyl ester and 150 ml of 60% strength acetic acid, 1α-O-benzyl-N-propionyl-demethylmuramyl-L-alanyl-D-glutamic acid ($C_\alpha$)-tert.-butyl ester-($C_\gamma$)-benzyl ester in the form of colourless crystals having a melting point of 152°–153° (from methanol:water=1:5); $[\alpha]_D^{20}=+68.9\pm0.1°$ (c=0.991; methanol), $R_f=0.40$ (chloroform:methanol=9:1) and $R_f=0.70$ (acetonitrile:water=3:1).

The starting product is obtained as follows:

Analogously to Example 13 there is obtained, from 4.65 g (9.62 mmol, 2.066 mmol/g, still contains sodium chloride) of the sodium salt of 1α-O-benzyl-4,6-O-isopropylidene-N-propionyl-demethylmuramic acid, 2.38 g (11.54 mmol) of dicyclohexyl carbodiimide, 1.33 g (11.54 mmol) of N-hydroxysuccinimide and 3.86 g (9.62 mmol) of L-alanyl-D-glutamic acid ($C_\alpha$)-tert.-butyl ester-($C_\gamma$)-benzyl ester hydrochloride, 1α-O-benzyl-4,6-O-isopropylidene-N-propionyl-demethylmuramyl-L-alanyl-D-glutamic acid ($C_\alpha$)-tert.-butyl ester-($C_\gamma$)-benzyl ester containing 0.31 mol of water; $[\alpha]_D^{20} = +38.4 \pm 0.1°$ (c=1.086; methylene chloride), $R_f=0.86$ (acetonitrile:water=3:1) and $R_f=0.83$ (chloroform:methanol=9:1).

EXAMPLE 15

Analogously to Example 13 there is obtained, from 3.07 g (4 mmol) of crude (still contains some dicyclohexyl urea) N-propionyl-demethylmuramyl-L-alanyl-D-glutamic acid $(C_\alpha)$-n-butyl ester-$(C_\gamma)$-N-hydroxysuccinimide ester and 2.37 g (3.1 mmol) of L-alanine-2-(1,2-dipalmitoyl-sn-glycero-3-hydroxyphosphoryloxy)-ethylamide, the sodium salt of N-propionyl-demethylmuramyl-L-alanyl-D-glutamyl-$(C_\alpha)$-n-butyl ester-$(C_\gamma)$-L-alanine-2-(1,2-dipalmitoyl-sn-glycero-3-hydroxyphosphoryloxy)-ethylamide in the form of a colourless powder containing 2.93 mol of water: $[\alpha]_D^{20} = +6.9 \pm 0.1°$ (c=0.504; methylene chloride), $R_f=0.65$ (chloroform:methanol:water=70:30:5) and $R_f=0.63$ (chloroform:methanol=7:3).

The starting material is obtained as follows:

Analogously to Example 13 there is obtained, from 2.2 g (3.9 mmol) of N-propionyl-demethylmuramyl-L-alanyl-D-glutamic acid α-n-butyl ester, 1.2 g (5.8 mmol) of dicyclohexyl carbodiimide and 0.69 g (5.8 mmol) of N-hydroxysuccinimide, crude N-propionyl-demethylmuramyl-L-alanyl-D-glutamic acid $(C_\alpha)$-n-butyl ester-$(C_\gamma)$-N-hydroxysuccinimide ester in the form of colourless crystals, which in fact still contain some dicyclohexyl urea and are used without being further purified; $R_f=0.66$ (chloroform:methanol:water=70:30:5).

The starting material is obtained as follows:

Analogously to Example 14 (hydrogenation time 20 minutes) there is obtained, from 7.3 g (11.3 mmol) of N-propionyl-demethylmuramyl-L-alanyl-D-glutamic acid $(C_\alpha)$-n-butyl ester-$(C_\gamma)$-benzyl ester, N-propionyl-demethylmuramyl-L-alanyl-D-glutamic acid α-n-butyl ester in the form of a colourless powder containing 0.88 mol of water; $[\alpha]_D^{20} = +16.4 \pm 0.1°$ (c=0.959; water), $R_f=0.61$ (methylene chloride:methanol:water=70:30:5) and $R_f=0.52$ (acetonitrile:water=3:1).

The starting material is obtained as follows:

In an analogous manner to that described in Example 13 there is obtained, from 9.5 g (13.97 mmol) of 4,6-O-isopropylidene-N-propionyl-demethylmuramyl-L-alanyl-D-glutamic acid $(C_\alpha)$-n-butyl ester-$(C_\gamma)$-benzyl ester and 120 ml of 60% strength acetic acid, N-propionyl-demethylmuramyl-L-alanyl-D-glutamic acid $(C_\alpha)$-n-butyl ester-$(C_\gamma)$-benzyl ester containing 0.41 mol of water; $[\alpha]_D^{20} = +15.7 \pm 0.1°$ (c=1.019; methanol), $R_f=0.23$ (methylene chloride:methanol=9:1), $R_f=0.45$ (methylene chloride:methanol=5:1) and $R_f=0.82$ (methylene chloride:methanol:$H_2O$=70:30:5).

The starting product is obtained as follows:

In an analogous manner to that described in Example 13 there is obtained, from 3.81 g (10.76 mmol, 2.72 mmol/g, still contains sodium chloride) of the sodium salt of 4,6-O-isopropylidene-N-propionyl-demethylmuramic acid, 2.44 g (11.83 mmol) of dicyclohexyl carbodiimide, 1.36 g (11.83 mmol) of N-hydroxysuccinimide and 4.3 g (10.76 mmol) of L-alanyl-D-glutamic acid $(C_\alpha)$-n-butyl ester-$(C_\gamma)$-benzyl ester hydrochloride, 4,6-O-isopropylidene-N-propionyl-demethylmuramyl-L-alanyl-D-glutamic acid $(C_\alpha)$-n-butyl ester-$(C_\gamma)$-benzyl ester; $[\alpha]_D^{20} = +10.6 \pm 0.1°$ (c=0.928; methanol), $R_f=0.81$ (methylene chloride:methanol:water=70:30:5) and $R_f=0.57$ (methylene chloride:methanol:=5:1).

EXAMPLE 16

28 ml of trifluoroacetic acid are added to a solution in 112 ml of absolute methylene chloride of 2.85 g (2.09 mmol) of the sodium salt of N-propionyl-demethylmuramyl-L-alanyl-D-glutamyl-$(C_\alpha)$-tert.-butyl ester-$(C_\gamma)$-L-alanine-2-(1,2-dipalmitoyl-sn-glycero-3-hydroxyphosphoryloxy)-ethylamide obtained according to Example 14, and the whole is stirred for 3 hours at room temperature.

The colourless clear solution is then concentrated by evaporation in vacuo at 30° and the resulting residue is repeatedly taken up in methylene chloride and concentrated by evaporation again.

3.0 g of a colourless oil are obtained which, dissolved in 350 ml of phosphate buffer/sodium chloride (each 0.1 molar, 1:1, pH 7), is filtered at 3 atmospheres gauge in an AMICON dialysis cell (model 402, ultrafilter PM 30/76 mm φ). The product is then filtered further, using a total of 2.1 liters of bidistilled water, until free from chloride. The solution remaining in the cell (approximately 50 ml) is lyophilised in a high vacuum.

A colourless lyophilisate is obtained, which is further purified by column chromatography over 260 g of silica gel (60 high-purity, Merck, 0.063–0.200 mm) in the system chloroform:methanol:water 70:30:5 (10 ml fractions).

Fractions 90–260 are combined and concentrated to dryness by evaporation in a high vacuum without heating (cooling). The residue is taken up in 250 ml of bidistilled water and in an AMICON dialysis cell (model 402, ultrafilter PM 30/76 mm φ) first concentrated at 3 atmospheres gauge to approximately 50 ml, then filtered until free from chloride using, in succession, 250 ml of phosphate buffer/sodium chloride (each 0.1 molar, 1:1, pH 7) and 1750 ml of bidistilled water. The solution remaining in the cell is then sterile-filtered through two millipore filters (NALGENE S, 0.45μ and 0.2μ) and lyophilised in a high vacuum.

The disodium salt of N-propionyl-demethylmuramyl-L-alanyl-D-glutamic acid $(C_\gamma)$-L-alanine-2-(1,2-dipalmitoyl-sn-glycero-3-hydroxyphosphoryloxy)-ethylamide is obtained in the form of a colourless hygroscopic powder containing 4.80 mol of water; $[\alpha]_D^{20} = +6.1 \pm 0.1°$ (c=0.489; methylene chloride:ethanol=1:1), $R_f=0.28$ (ethyl acetate:n-butanol:pyridine:acetic acid:water=42:21:21:6:10) and $R_f=0.62$ (acetonitrile:water=3:1).

EXAMPLE 17

4.5 g (34 mmol) of the sodium salt of N-acetylmuramyl-L-alanyl-D-glutamyl-$(C_\alpha)$-tert.-butyl ester-$(C_\gamma)$-L-alanine-2-(1,2-dipalmitoyl-sn-glycero-3-hydroxyphosphoryloxy)-ethylamide obtained according to Example 12, which have been dried in a high vacuum over phosphorus pentoxide, are dissolved in 75 ml of dry dichloromethane. The solution is cooled to 0° and, while stirring and with the exclusion of moisture, 25 ml of anhydrous trifluoroacetic acid are added thereto and the whole is allowed to warm up to room temperature. After 2½ hours, the clear colourless solution is substantially concentrated (~10 ml) in a rotary evaporator at room temperature and, repeatedly, 100 ml of dichloromethane are added and evaporated off again. The remaining oil is taken up in 100 ml of tert.-butanol and lyophilised. The crude product is purified by chromatography twice, each time over 400 g of silica gel 60 in the system chloroform:methanol:water=80:30:5. The material contained in fractions 92-172 is dissolved in 100 ml of double-distilled water and purified by diafiltration (AMICON stirrer cell 402, ultrafilter PM 10/76 mm φ) analogously to Example 1. The solution remaining in the cell is filtered through a millipore filter (0.2μ) and lyophilised.

The disodium salt of N-acetylmuramyl-L-alanyl-D-glutamic acid $(C_\gamma)$-L-alanine-2-(1,2-dipalmitoyl-sn-glycero-3-hydroxyphosphoryloxy)-ethylamide containing 4.89 mol of water is obtained in the form of a loose colourless powder; $[\alpha]_D^{20} = +10 \pm 1°$ (c=0.675; methanol), $R_f$=0.08 (chloroform:methanol:water=70:30:5), $R_f$=0.15 (ethyl acetate:n-butanol-pyridine:acetic acid:water=42:21:21:6:10) and $R_f$=0.30 (chloroform:methanol:water:acetic acid=70:40:9:1).

EXAMPLE 18

Alveolar rat macrophages are obtained by lung washing, plated out and incubated in vitro for 24 hours either with liposomes that are charged with the active ingredient, or with the active ingredient in physiological salt solution (phosphate buffered saline, PBS), $^{125}$I-marked tumour cells are added and incubation is continued for a further 72 hours. Subsequently the dead tumour cells are washed away and the number of tumour cells still living is determined on the basis of their radioactivity. The macrophage activation is assessed on the basis of the cytotoxicity, that is to say according to the proportion of animals dead at the end of the test. The specific cytotoxicity [%] is calculated as follows:

$$100 \left[ 1 - \frac{\text{cpm in tumour cells incubated with macrophages and active ingredient}}{\text{cpm in tumour cells incubated with macrophages and PBS}} \right]$$

Further details of the above-mentioned test method are described in I. J. Fidler et. al., *J. Biol. Response Modifiers* 1, 43-55 (1982). Some test results relating to the following active ingredients are compiled in the following Table:

I the sodium salt of N-acetylmuramyl-L-alanyl-D-glutamyl-$(C_\alpha)$-n-butyl ester-$(C_\gamma)$-L-alanine-2-(1,2-dipalmitoyl-sn-glycero-3-hydroxyphosphoryloxy)-ethylamide, II the sodium salt of N-propionylnormuramyl-L-alanyl-D-glutamyl-$(C_\alpha)$-n-butyl ester-$(C_\gamma)$-L-alanine-2-(1,2-dipalmitoyl-sn-glycero-3-hydroxyphosphoryloxy)-ethylamide, III the sodium salt of N-propionylnormuramyl-L-alanyl-D-glutamyl-$(C_\alpha)$-methyl ester-$(C_\gamma)$-L-alanine-2-(1,2-dipalmitoyl-sn-glycero-3-hydroxyphosphoryloxy)-ethylamide, and IV the sodium salt of N-acetylmuramyl-L-alanyl-D-glutamyl-$(C_\alpha)$-tert.-butyl ester-$(C_\gamma)$-L-alanine-2-(1,2-dipalmitoyl-sn-glycero-3-hydroxyphosphoryloxy)-ethylamide.

| | Specific cytotoxicity [%] | | | | | | | |
|---|---|---|---|---|---|---|---|---|
| | Active ingredient in 0.2 ml of PBS μg/culture | | | | Active ingredient in 100 μg of lipsomes per 0.2 ml μg/culture | | | |
| Active Ingredient | 0.02 | 0.2 | 2 | 20 | 0.02 | 0.2 | 2 | 20 |
| I | | 39 | 59 | | | 56 | 51 | 44 |
| II | | 21 | 48 | 74 | | 10 | 23 | 11 |
| III | 3 | 81 | 47 | | 64 | 76 | 79 | |

| | Specific cytotoxicity [%] | | | | | | | |
|---|---|---|---|---|---|---|---|---|
| | Active ingredient in 0.2 ml of PBS μg/culture | | | | Active ingredient in 100 μg of lipsomes per 0.2 ml μg/culture | | | |
| Active Ingredient | 0.02 | 0.2 | 2 | 20 | 0.02 | 0.2 | 2 | 20 |
| IV | | 23 | 18 | 20 | | 64 | 68 | 52 |

EXAMPLE 19

Manufacture of 1000 tablets containing 0.5% of active ingredient

| Composition for 1000 tablets: | |
|---|---|
| the sodium salt of N—acetylmuramyl-L-alanyl-D-glutamyl-$(C_\alpha)$-methyl ester-$(C_\gamma)$-L-alanine-2-(1,2-dipalmitoyl-sn-glycero-3-hydroxyphosphoryloxy)-ethylamide | 0.5 g |
| lactose, ground | 43.0 g |
| corn starch | 52.0 g |
| Pharmacoat 603 ® (hydroxypropylmethylcellulose containing 28–30% methoxy groups, supplied by Shinetsu Chemical Company, Tokyo, Japan) | 3.0 g |
| Aerosil ® (colloidal silica, supplied by Degussa, Frankfurt, Federal Republic of Germany) | 1.0 g |
| magnesium stearate | 0.5 g |

Preparation:

The active ingredient and 15 g of lactose are premixed. The resulting premix is mixed with 28 g of lactose and 47 g of corn starch. Using the resulting mixture and an aqueous solution of the Pharmacoat a composition suitable for granulation is prepared and this is granulated, dried and ground. 5 g of corn starch, the Aerosil and magnesium stearate are mixed in and the whole is pressed to form 1000 tablets each weighing 100 mg.

The compacts can be provided with a coating that is resistant to gastric juices in a manner known per se.

EXAMPLE 20

Active ingredient in the form of a dry lyophilised substance 1 mg of the sodium salt of N-acetylmuramyl-L-alanyl-D-glutamyl-$(C_\alpha)$-methyl ester-$(C_\gamma)$-L-alanine-2-(1,2-dipalmitoyl-sn-glycero-3-hydroxyphosphoryloxy)-ethylamide and 500 mg of mannitol (pyrogen-free) are dissolved in water for injection and sterile-filtered through a membrane filter. The sterile-filtered solution is introduced under aseptic conditions into a sterilised glass ampoule or into a glass phial and freeze-dried. After lyophilisation the ampoule is sealed or the phial is sealed with a rubber-elastomeric seal and aluminium cap.

We claim:

1. The compounds of the formula I

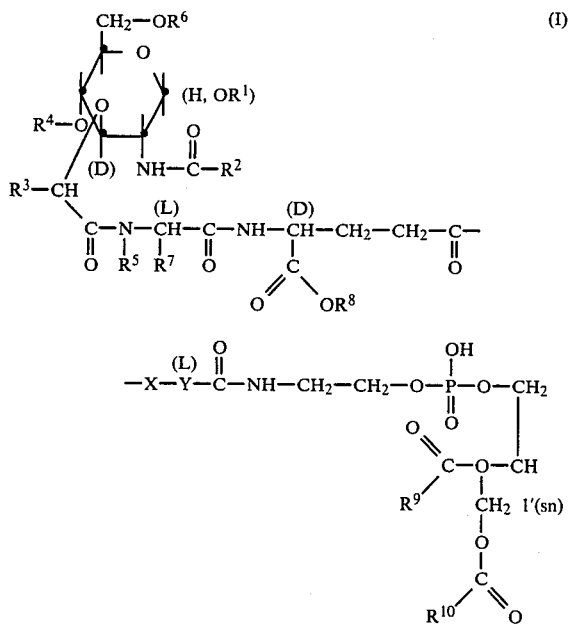

wherein
R[1], R[4] and R[6] are hydrogen, R[2] is methyl or ethyl, R[3] is hydrogen or methyl, R[5] is hydrogen, R[7] is methyl, R[8] is hydrogen or $C_1$–$C_4$-alkyl, X is the group NH, Y is ethylidene, and R[9] and R[10] are N-pentadecyl, and their pharmaceutically acceptable salts.

2. N-acetylmuramyl-L-alanyl-D-glutamyl-($C_\alpha$)-n-butyl ester-($C_\gamma$)-L-alanine-2-(1,2-dipalmitoyl-sn-glycero-3-hydroxyphosphoryloxy)-ethylamide and its pharmaceutically acceptable salts according to claim 1.

3. N-Propionyl-demethylmuramyl-L-alanyl-D-glutamyl-($C_\alpha$)-n-butyl ester-($C_\gamma$)-L-alanine-2-(1,2-dipalmitoyl-sn-glycero-3-hydroxyphosphoryloxy)-ethylamide and its pharmaceutically acceptable salts according to claim 1.

4. N-Acetylmuramyl-L-alanyl-D-glutamyl-($C_\alpha$)-methyl ester-($C_\gamma$)-L-alanine-2-(1,2-dipalmitoyl-sn-glycero-3-hydroxyphosphoryloxy)-ethylamide and its pharmaceutically acceptable salts according to claim 1.

5. N-Propionyl-demethylmuramyl-L-alanyl-D-glutamyl-($C_\alpha$)-methyl ester-($C_\gamma$)-L-alanine-2-(1,2-dipalmitoyl-sn-glycero-3-hydroxyphosphoryloxy)-ethylamide and its pharmaceutically acceptable salts according to claim 1.

6. Pharmaceutically acceptable salts according to claim 1.

7. Pharmaceutically acceptable salts according to claim 6.

8. Compounds according to claim 1, wherein R[8] is $C_1$–$C_4$-alkyl.

9. A compound according to claim 1 which is N-acetylmuramyl-L-alanyl-D-glutamyl-($C_\alpha$)-tert.-butyl ester-($C_\gamma$)-L-alanine-2-(1,2-dipalmitoyl-sn-glycero-3-hydroxyphosphoryloxy)-ethylamide and its pharmaceutically acceptable salts.

10. A compound according to claim 1 which is N-propionyl-demethylmuramyl-L-alanyl-D-glutamyl-($C_\alpha$)-tert.-butyl ester-($C_\gamma$)-L-alanine-2-(1,2-dipalmitoyl-sn-glycero-3-hydroxyphosphoryloxy)-ethyl-amide and its pharmaceutically acceptable salts.

11. A compound according to claim 1 which is N-propionyl-demethylmuramyl-L-alanyl-D-glutamic acid ($C_\gamma$)-L-alanine-2-(1,2-dipalmitoyl-sn-glycero-3-hydroxyphosphoryloxy)-ethylamide and its pharmaceutically acceptable salts.

12. A compound according to claim 1 which is N-acetylmuramyl-L-alanyl-D-glutamic acid ($C_\gamma$)-L-alanine-2-(1,2-dipalmitoyl-sn-glycero-3-hydroxyphosphoryloxy)-ethylamide and its pharmaceutically acceptable salts.

13. Sodium salts according to claim 8.

14. Pharmaceutical preparations for stimulating the immune system of warm-blooded animals including humans that contain an immunostimulatory effective amount of a compound according to claim 1 together with a significant amount of a pharmaceutical carrier.

15. Pharmaceutical preparations for stimulating the immune system of warm-blooded animals including humans that contain an immunostimulatory effective amount of a compound according to claim 8 together with a significant amount of a pharmaceutical carrier.

16. Method of stimulating the immune system of warm-blooded animals including humans by administering to said animals in need of such treatment an effective amount of a compound according to claim 1.

17. Method of prophylaxis and treatment of warm-blooded animals including humans in the case of virus infections by administering to said animals in need of such treatment an effective amount of a compound according to claim 1.

* * * * *

UNITED STATES PATENT AND TRADEMARK OFFICE
CERTIFICATE OF CORRECTION

PATENT NO. : 4,548,923

DATED : October 22, 1985

INVENTOR(S) : Albert Hartman et al

It is certified that error appears in the above-identified patent and that said Letters Patent is hereby corrected as shown below:

On the title page, in the Abstract, Column 1, lines 10-34 and Column 45, lines 1-25, the structural formula should appear as shown on the attached sheet.

Signed and Sealed this

Sixth Day of January, 1987

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,548,923

DATED : October 22, 1985

INVENTOR(S) : Albert Hartman et al.

Page 2 of 2

It is certified that error appears in the above-identified patent and that said Letters Patent is hereby corrected as shown below:

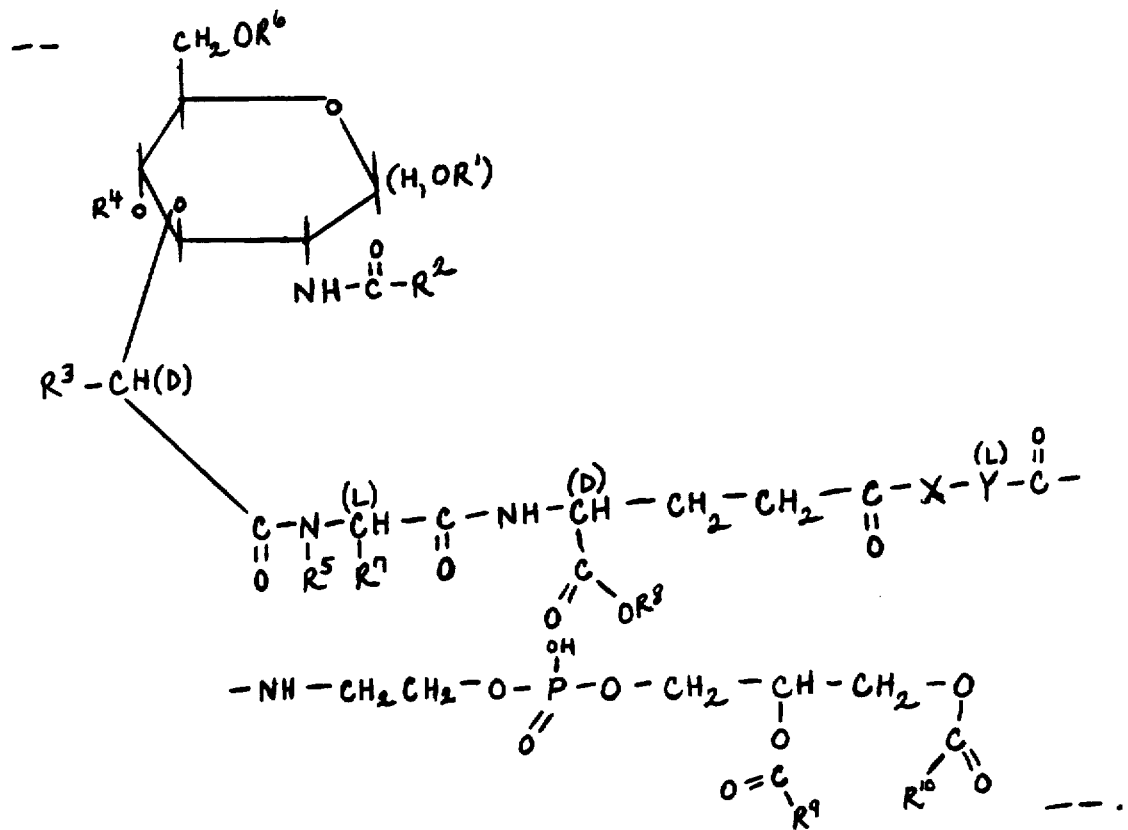

UNITED STATES PATENT AND TRADEMARK OFFICE
CERTIFICATE OF CORRECTION

PATENT NO. : 4,548,923

DATED : October 22, 1985

INVENTOR(S) : Albert Hartmann, Oskar Wacker, Gerhard Baschang and Lajos Tarcsay

It is certified that error appears in the above-identified patent and that said Letters Patent is hereby corrected as shown below:

On the cover page: change the priority date of Swiss Patent Application No. 4527/82 of "June 21, 1982" to --July 23, 1982--.

Signed and Sealed this

Thirteenth Day of December, 1988

*Attest:*

DONALD J. QUIGG

*Attesting Officer*  *Commissioner of Patents and Trademarks*